United States Patent [19]

Evans

[11] Patent Number: 4,937,331
[45] Date of Patent: Jun. 26, 1990

[54] CHIRAL AZETIDINONE EPOXIDES

[75] Inventor: David A. Evans, Concord, Mass.

[73] Assignee: President and Fellows of Harvard College, Cambridge, Mass.

[21] Appl. No.: 173,381

[22] Filed: Mar. 25, 1988

[51] Int. Cl.$^5$ .................. C07D 405/14; C07D 405/04; C07D 413/14; C07F 9/65

[52] U.S. Cl. .................................................. 540/364

[58] Field of Search ........................................ 540/364

[56] References Cited

U.S. PATENT DOCUMENTS

| 4,471,130 | 9/1984 | Katsuki et al. | 549/523 |
| 4,594,439 | 6/1986 | Katsuki et al. | 549/523 |
| 4,699,986 | 10/1987 | Hubschwerlen et al. | 549/451 |

FOREIGN PATENT DOCUMENTS 59-176286 10/1984 Japan .

OTHER PUBLICATIONS

Gigg, Carbohydrate Research, 100, C5-9, (1982).
Fakuyama, Chem. Abs. 102, 78618(b) 1984.
"Protecting Groups in Organic Chemistry" (1981), Green, ed., p. 268.
Kyowa, Chem. Abs. 102, 113170y (1982), and index entry sheet.
S. Uyeo et al., "Synthesis of 1-Carbacephem Derivatives", Chem. Pharm. Bull., 28 (5) 1563-1577 (1980).

Primary Examiner—Mark L. Berch
Attorney, Agent, or Firm—William B. Scanlon; Leroy Whitaker

[57] ABSTRACT

Epoxyimines, formed from epoxyaldehydes, react via cycloaddition with amino-protected glycyl halides to provide 3-protected-amino-4-(substituted oxiranyl)azetidinones represented by the formula

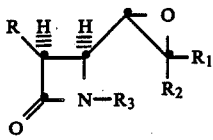

wherein, e.g., R is protected amino; $R_1$ and $R_2$ is H, alkyl, phenyl, etc.; and $R_3$ inter alia a nitrogen-protecting group. Chiral epoxyimines from chiral epoxyaldehydes induce high levels of asymmetric induction during the cycloaddition to provide substantially one diastereomer of the 3,4-disubstituted azetidinone. For example, the epoxyimine formed with (2R,3S)-2-formyl-3-phenyloxirane and 2,4-dimethoxybenzylamine is reacted with phthalimidoacetyl chloride to provide [3R,4R,4(2S,3S)]-1-(2,4-dimethoxybenzyl)-3-phthalimido-4-(3-phenyloxiran-2-yl)-2-azetidinone.

The epoxy-substituted azetidinones are useful intermediates for β-lactam antibiotic compounds.

24 Claims, No Drawings

CHIRAL AZETIDINONE EPOXIDES

The United States government has rights in this invention by virtue of Grant No. GM-33328 awarded by the National Institutes of Health.

BACKGROUND OF THE INVENTION

This invention relates to β-lactam antibiotics. In particular, it relates to chiral β-lactam intermediates and to a process for the preparation thereof.

The penicillin and cephalosporin antibiotics can be considered as classical β-lactam antibiotics. In recent years other monocyclic and bicyclic β-lactam antibiotic compounds and β-lactamase inhibitory compounds have been discovered such as the mono-bactams, clavulanic acid, thienamycin, and the 1-carba(1-dethia)cephalosporin compounds. Considerable effort has been devoted to the development of preparative methods for the synthesis of these nonclassical β-lactam compounds. In particular, asymmetric preparative methods have undergone considerable study. Among the more efficient methods for constructing the β-lactam ring is the so-called keteneimine cycloaddition comprising the reaction of an amino-protected glycyl chloride or other ketene generating derivative with an imine in the presence of a tertiary amine. For example, Evans et al., U.S. Pat. No. 4,665,171, describe an asymmetric method for preparing the β-lactam ring which comprises the cycloaddition of an imine with a chiral 4-(S)-aryloxazolidin-2-one-3-yl acetyl halide wherein the aryloxazolidinone functions as the chiral auxiliary. According to the process of this invention, the chirality of the β-lactam ring is induced with a chiral epoxyaldehyde employed to form the imine for use in the cycloaddition.

SUMMARY OF THE INVENTION

Chiral 2,3-epoxyaldehydes can be converted to imines for cycloaddition with amino-protected glycyl derivatives, for example acid halides, to provide chiral azetidinones represented by the following formula 1.

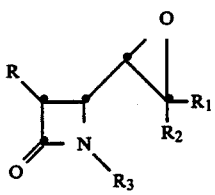

wherein R is amino, substituted amino, azido, alkyl, substituted alkyl or acyl; $R_1$ and $R_2$ independently are hydrogen or groups such as alkyl or aryl; and $R_3$ is inter alia a nitrogen-protecting group.

The azetidinones represented by formula 1 are useful intermediates for the preparation of monocyclic and bicyclic β-lactam antibiotics.

DETAILED DESCRIPTION

The azetidinone compounds provided by this invention are represented by the following formula 1.

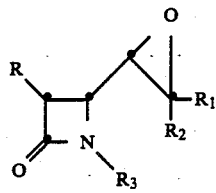

wherein R is amino, protected amino or azido;

$R_1$ and $R_2$ independently are hydrogen, $C_1$–$C_6$ alkyl, $C_3$–$C_8$ cycloalkyl, —$COOR_3'$ wherein $R_3'$ is a carboxy-protecting group, tri-($C_1$–$C_4$ alkyl)silyl, tri-($C_1$–$C_4$ alkyl)silyloxy, cyano, a group of the formula —$CH_2OR_3''$ wherein $R_3''$ is $C_1$–$C_4$ alkyl, $C_1$–$C_5$ alkanoyl, $C_1$–$C_4$ alkylsulfonyl or tri-($C_1$–$C_4$ alkyl)silyl; phenyl, substituted phenyl, naphthyl, substituted naphthyl or a heteroaryl group selected from thienyl, furyl, benzofuryl, benzothienyl or substituted heteroaryl;

$R_3$ is a nitrogen-protecting group, a substituted methyl group represented by the formula

—CH($R_4$)$COOR_3'$ wherein $R_3'$ is a carboxy-protecting group; $R_4$ is hydrogen, —$COOR_3'$ wherein $R_3'$ has the same meaning as above, or a phosphono group represented by the formula —$P(O)(OR_5)_2$ wherein $R_5$ is $C_1$–$C_4$ alkyl, phenyl or benzyl and phenyl or benzyl substituted by $C_1$–$C_4$ alkyl, $C_1$–$C_4$ alkoxy or halogen; or $R_3$ is an alkenyl group represented by the formula

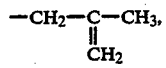

or a β-keto ester derivative represented by the formula

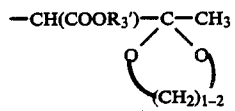

wherein $R_3'$ has the same meaning as defined above.

As used in the above formula 1, the term "protected amino" refers to the amino group substituted with a conventional amino-protecting group or blocking group used for the temporary protection of the basic amino group. Examples of such R groups include phthalimido, 4,5-diphenyl-4-oxazolin-2-one-3-yl ("Ox"), an imine group such as is formed with an aromatic aldehyde, e.g., benzaldehyde (benzylidene), an enamine group such as one formed with methyl or ethyl acetoacetate, or a urethane group represented by the formula

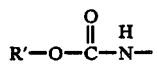

wherein R' is $C_1$–$C_{12}$ alkyl, halo-substituted $C_1$–$C_{12}$ alkyl, $C_3$–$C_{12}$ alkenyl, $C_3$–$C_8$ cycloalkyl, adamantyl, diphenylmethyl, benzyl, substituted benzyl substituted by methoxy, $C_1$–$C_6$ alkyl, halogen or nitro. Examples of the latter type include methoxycarbonylamino, ethoxycarbonylamino, t-butyloxycarbonylamino, t-amyloxycarbonylamido, 2,2,2-trichloroethoxycarbonylamino, allyloxycarbonylamino, cyclopentyloxycarbonylamino, cyclohexyloxycarbonylamino, adamantyloxycarbonylamino, benzyloxycarbonylamino, p-nitrobenzyloxycarbonylamino, and diphenylmethoxycarbonylamino.

Preferred protected amino groups of the invention are phthalimido, 4,5-diphenyloxazolin-2-one-3-yl (Ox), and benzyloxycarbonylamino (Cbz) or a substituted benzyloxycarbonylamino group.

The term "$C_1$-$C_6$ alkyl" refers to the straight and branched chain alkyl groups such as methyl, ethyl, n-propyl, n-butyl, iso-propyl, sec-butyl, n-pentyl, n-hexyl, and like alkyl groups.

The term "$C_3$-$C_8$ cycloalkyl" refers to cyclopropyl, cyclobutyl, cyclopentyl, cyclohexyl, cycloheptyl and cyclooctyl.

The terms "tri-($C_1$-$C_4$ alkyl)silyl" and "tri-($C_1$-$C_4$ alkyl)silyloxy" refer to the straight chain and branched chain alkyl substituted silyl and silyloxy groups wherein the alkyl groups are the same or are mixed. Examples include trimethylsilyl, trimethylsilyloxy, triethylsilyl, dimethyl-t-butylsilyl, diethyl-t-butylsilyloxy and the like.

The term "$C_1$-$C_5$ alkanoyl" refers to the straight and branched chain alkanoyl groups such as formyl, acetyl, propionyl, butyryl, pivaloyl and the like.

The term "$C_1$-$C_4$ alkylsulfonyl" refers to such groups as methylsulfonyl, ethylsulfonyl, or butylsulfonyl and the like.

The term "substituted phenyl" refers to the phenyl group substituted by one or more, preferably one or two, of the same or different groups selected from among $C_1$-$C_4$ alkyl, $C_1$-$C_4$ alkoxy, halogen, protected amino, di-($C_1$-$C_4$ alkyl)amino, protected carboxy, $C_1$-$C_5$ *alkanoyloxy*, $C_1$-$C_4$ alkylsulfonyloxy, $C_1$-$C_4$ alkylsulfonyl, phenylsulfonyl or phenylsulfonyl substituted on phenyl by $C_1$-$C_4$ alkyl, $C_1$-$C_4$ alkoxy or halogen.

The term "substituted naphthyl" refers to 1- or 2-naphthyl substituted on one or both rings by one or two of the same or different groups defined hereinabove for the term "substituted phenyl".

The term "substituted heteroaryl" refers to thienyl, furyl, benzothienyl or benzofuryl substituted by one or two of the same or different groups defined hereinabove for the term "substituted phenyl".

The term "nitrogen-protecting group" refers herein to groups commonly employed to block the azetidinone nitrogen atom. Examples of such nitrogen-protecting groups include benzyl, 4-methoxybenzyl, 2,4-dimethoxybenzyl, 4-methoxyphenyl, 3,4-dimethoxyphenyl, trialkylsilyl groups for example trimethylsilyl, triethylsilyl, t-butyldimethylsilyl, and like nitrogen-protecting groups.

The group $R_3$ also represents non-nitrogen protecting groups which may be used in subsequent synthetic steps to elaborate a ring fused to the $\beta$-lactam ring. Illustrative of such groups when $R_3$ is —CH($R_4$)COOR$_3'$ and $R_4$ is hydrogen are benzyloxycarbonylmethyl, t-butyloxycarbonylmethyl, trimethylsilyloxycarbonylmethyl, dimethyl-t-butylsilyloxycarbonylmethyl, diphenylmethoxycarbonylmethyl and the like; and when $R_4$ is COOR$_3'$, di-(ethoxycarbonyl)methyl, di-(trimethylsilyloxycarbonyl)methyl, di(benzyloxycarbonyl)methyl, di-(4-methoxybenzyloxycarbonyl)methyl and the like; and when $R_4$ is a phosphono group, (dimethylphosphono)-t-butyloxycarbonylmethyl, (dimethylphosphono)benzyloxycarbonylmethyl, (diphenylphosphono)-4-methoxybenzyloxycarbonylmethyl, [di-(4-chlorophenyl)phosphono]trimethylsilyloxycarbonylmethyl and the like. The $\alpha$-keto ester derivative group represented by $R_3$ is exemplified by the ketals formed with ethylene glycol and propylene glycol and the $\beta$-ketoesters, 1-(benzyloxycarbonyl)prop-2-one-1-yl, 1-(4-methoxybenzyloxycarbonyl)prop-2-one-1-yl, 1-(t-butyloxycarbonyl)prop-2-one-1-yl and like groups.

The term "carboxy-protecting group", as used herein refers to groups conventionally employed in the $\beta$-lactam art for the temporary protection of the carboxy group. Examples of such groups include $C_1$-$C_4$ alkyl, e.g., t-butyl; haloalkyl groups, e.g., 2,2,2-trichloroethyl or 2-iodoethyl; allyl; benzyl, 4-methoxybenzyl, 4-nitrobenzyl, diphenylmethyl; trialkylsilyl or mixed alkylarylsilyl groups, e.g., trimethylsilyl, triethylsilyl, dimethylphenylsilyl, t-butyldimethylsilyl, $\beta$-(trimethylsilyl)ethyl or $\beta$-(t-butyldimethylsilyl)ethyl; 2-methylsulfonylethyl; and like ester groups.

Examples of the esterified carboxy group —COOR$_3'$ defined for formula 1 include t-butyloxycarbonyl, benzyloxycarbonyl, diphenylmethoxycarbonyl, 2,2,2-trichloroethoxycarbonyl, p-methoxybenzyloxycarbonyl, p-nitrobenzyloxycarbonyl, trimethylsilyloxycarbonyl, t-butyldimethylsilyloxycarbonyl, $\beta$-(trimethylsilyl)ethoxycarbonyl and 2-methylsulfonylethoxycarbonyl.

Examples of the group —CH$_2$OR$_3''$ represented by $R_1$ and $R_2$ in formula 1 are methoxymethyl, ethoxymethyl, acetoxymethyl, t-butyloxymethyl, pivaloyloxymethyl, methylsulfonyloxymethyl, p-toluenesulfonyloxymethyl, trifluoromethylsulfonyloxymethyl, trimethylsilyloxymethyl and like groups.

The azetidinones represented by the above formula 1 are cis-azetidinones which are provided in high yield in either diastereomeric form via an asymmetric cycloaddition process. According to the process, an acid derivative, e.g., an amino-protected glycine derivative or an azidoacetic acid derivative is reacted with a chiral epoxy imine to form the compound represented by formula 1 as shown in the reaction scheme below.

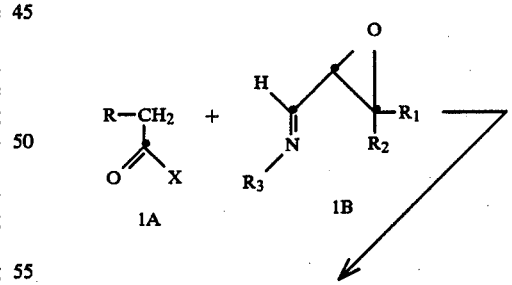

In the above reaction scheme, R is other than amino; X refers to halogen, preferably chloro or bromo, trifluoroacetoxy or —OP(O)X$_2$, wherein X is chloro or bromo; and $R_1$, $R_2$ and $R_3$ have the same meanings as defined for formula 1.

The process is carried out in an inert solvent at a temperature between about $-80°$ C. and about $0°$ C. in the presence of a tertiary imine.

A key feature of the process comprises the use of a chiral epoxyaldehyde to form the epoxy imine as shown below.

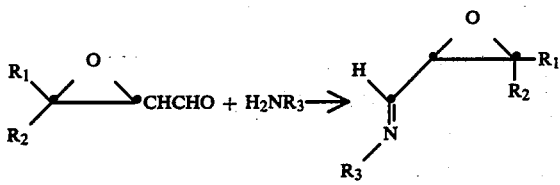

The chiral epoxy group of the imine affords high levels of asymmetric induction during the cycloaddition to provide a high degree of stereoselectivity in the formation of the 3,4-disubstituted azetidinone.

Inert solvents which can be employed in the process include the halogenated hydrocarbons such as methylene chloride, chloroform, di- or trichloro ethane and the like; aromatic hydrocarbons such as toluene; and ethers such as diethyl ether, tetrahydrofuran and the like. Tertiary amines such as the tri-($C_1$-$C_4$ alkyl) amines, for example triethylamine, are used in the process when the amino-protected glycine derivative is an acid halide such as the acid chloride. The formal cycloaddition reaction is carried out under substantially anhydrous conditions and, accordingly, the reactants and the solvents employed in the reaction are dried prior to use.

Preferably, an amount of imine slightly in excess of the stoichiometric amount (1:1) is used.

In carrying out the process, usually the imine is added to the cold solution of the acid derivative containing the tertiary amine. However, as with most processes, conditions and order of addition of reactants can vary for best results. For example, the azetidinone 1, wherein R is phthalimido, is best prepared by adding a solution of the desired imine to a cold (−78° C.) solution of phthalimidoacetyl chloride and the tertiary amine. When R is benzyloxycarbonylamino (Cbz protected amino), best results are obtained when the Cbz protected glycyl chloride is added to a cold (−10° C.) solution of the imine and the tertiary amine.

The chiral epoxy aldehydes represented by the formula

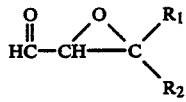

which are used in the preparation of the epoxy imine are obtained by the oxidation of the corresponding chiral epoxy alcohol. The latter are obtained by the metal-catalyzed asymmetric epoxidation of an allylic alcohol, for example as described by Sharpless et al. in *J. Am. Chem. Soc.* 1987, 109, 5765–5780. According to the Sharpless epoxidation method, an allylic alcohol is oxidized with t-butyl hydroperoxide in the presence of titanium tetraisopropoxide and a (+)- or (−)-dialkyl tartrate. Tartrates which have been employed in the epoxidation are diethyl tartrate or diisopropyl tartrate. The epoxy alcohol enantiomer is then oxidized to the corresponding aldehyde, preferably by employing standard Swern oxidation conditions. Alternatively, the aldehyde can be prepared with the chiral epoxy alcohol by oxidation with pyridine/sulfur trioxide or via Collins oxidation with chromium trioxide and pyridine. In an example of the preparation of a chiral aldehyde under Swern oxidation conditions, a solution of oxalyl chloride in dichloromethane is cooled to −78° C. and a solution of dimethylsulfoxide in dichloromethane added dropwise while the temperature is maintained below about −60° C. To the cold solution is added (2R-trans)-3-phenyloxiranemethanol (epoxycinnamyl alcohol). Triethylamine is then added and the reaction mixture maintained at a temperature of −78° C. for one hour. The mixture is allowed to warm to 0° C. over a period of about 30 minutes. The reaction mixture is diluted with water and the organic layer separated, washed and evaporated under vacuum to yield the unpurifed chiral aldehyde, (2S,3R)-2-formyl-3-phenyloxirane. The chiral epoxy aldehyde is purified by chromatography over silica gel. Oxidation of the chiral epoxy alcohol to the chiral epoxy aldehyde with chromium trioxide and pyridine or with pyridine and sulfur trioxide provides somewhat lower yields than those obtained under Swern oxidation conditions; however, the product is obtained in greater purity.

The chiral epoxy aldehydes provided by this invention have been found to be stable to silica gel chromatography and can be stored for several weeks at −20° C. under nitrogen without significant decomposition.

Examples of typical chiral epoxy aldehydes which can be used to form the imine in the cycloaddition reaction are listed below.

(S)-2-formyloxirane,
(S)-2-formyl-3,3-dimethyloxirane,
(R)-2-formyl-3,3-dimethyloxirane,
(R)-2-formyl-3,3-diethyloxirane,
(2R,3R)-formyl-3-n-butyloxirane,
(2R,3S)-2-formyl-3-phenyloxirane,
(2S,3R)-2-formyl-3-phenyloxirane,
(2S,3R)-2-formyl-3-(4-chlorophenyl)oxirane,
(2S,3R)-2-formyl-3-(3,4-dichlorophenyl)oxirane,
(2S,3R)-2-formyl-3-(4-methoxyphenyl)oxirane,
(2S,3R)-2-formyl-3-(2-naphthyl)oxirane,
(2S,3R)-2-formyl-3-(2-furyl)oxirane,
(2S,3R)-2-formyl-3-(trimethylsilyloxymethyl)oxirane,
(2S,3R)-2-formyl-3-(pivaloyloxymethyl)oxirane,
(S)-2-formyl-3,3-trimethylsilyloxirane,
(2S,3R)-2-formyl-3-cyanooxirane,
(2S,3R)-2-formyl-3-t-butyloxycarbonyloxirane, and
(2S,3R)-2-formyl-3-ethoxycarbonyloxirane.

The chiral epoxy imine used in the cycloaddition to form a compound of formula 1 is prepared in a conventional manner by condensing the chiral epoxy aldehyde with the amine $R_3NH_2$ wherein $R_3$ has the same meaning as defined hereinabove. As with the formation of other imines, a means for removing water resulting from imine formation is provided. For example, water may be removed by azeotropic distillation or, preferably, with a drying agent. In a typical procedure for formation of the chiral epoxy imine, a solution of the chiral epoxy aldehyde in an inert solvent such as dichloromethane is added to a solution of the amine in the same solvent and molecular sieves, preferably in pellet form, are added to the mixed solutions. The mixture is allowed to stand until imine formation is complete. The mixture is filtered to remove the insoluble sieves and the imine is isolated. Preferably, the filtrate containing the epoxy imine is used directly in the cycloaddition reaction without isolation.

The amines $R_3NH_2$ used in formation of the imine are available compounds or are obtained by known methods. Examples of such amines are aniline, 4-methoxyaniline, benzylamine, 4-methoxybenzylamine, 2,4-dimethoxybenzylamine, methallylamine, t-butyl glycinate, diethylaminomalonate, t-butyl α-(dimethylphosphono)-glycinate, 4-methoxybenzyl (α-diethylphosphono)-glycinate and benzyl α-(diphenylphosphono)glycinate.

Examples of epoxy imines which can be used to prepare the chiral azetidinones of formula 1 are listed below, wherein the headings have reference to formula 1B hereinabove.

| R₁ | R₂ | R₃ |
|---|---|---|
| H | H | 4-methoxyphenyl |
| CH₃ | CH₃ | benzyl |
| CH₃ | CH₃ | 2,4-dimethoxybenzyl |
| C₆H₅ | H | 4-methoxyphenyl |
| C₆H₅ | H | t-butyloxycarbonylmethyl |
| C₂H₅ | H | 2,4-dimethoxybenzyl |
| Furyl | H | benzyl |
| C₂H₅ | C₂H₅ | 4-methoxyphenyl |
| n-C₃H₇ | H | 2,4-dimethoxybenzyl |
| C₆H₅ | H | methallylamine |
| CN | H | 2,4-dimethoxybenzyl |
| COOC₂H₅ | H | benzyl |
| Si(CH₃)₃ | H | 4-methoxyphenyl |

The cis-azetidinones represented by formula 1 are obtained in the process of this invention with high diastereoselectivity. The chiral 2,3-epoxy aldehyde having the (2S) configuration is obtained with the precursor epoxy alcohol formed via Sharpless epoxidation with a D-(−)tartaric acid diester. The (2S)-epoxy aldehyde provides the azetidinone of formula 1 having the natural configuration of the cephalosporin antibiotics as shown in the following formula.

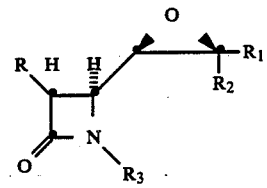

Alternatively, the process carried out with a chiral imine formed with a 2,3-epoxy aldehyde possessing the (2R) configuration provides the diastereomer represented by the following formula

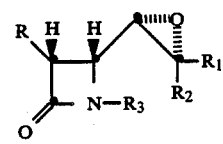

The cis-azetidinones of formula 1 are also provided in racemic form. The racemic form is obtained via cycloaddition with an imine formed with a racemic epoxy aldehyde. The racemic 1 may be converted to an antibiotic in racemic form or, alternatively, to an antibiotic which can be separated into diastereomeric forms.

The preferred process of this invention provides the cis-azetidinone (formula 1) in substantially one diastereoisomeric form by use of a chiral epoxyimine. The principal diastereomer from each reaction may be purified by either chromatography or direct crystallization in many instances.

The stereoselective nature of the preferred process is shown in Table 1 wherein the results obtained with the two chiral epoxyimines shown below are listed.

TABLE 1

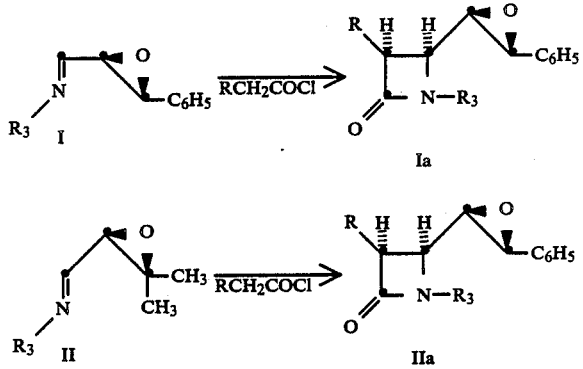

Ketene-Imine Cycloadditions of Epoxyimines I and II

| Imine | R | R₃ | Ratio[1] | Yield, %[2] | Mp, °C. |
|---|---|---|---|---|---|
| II | phthalimido | benzyl | 97:3 | 84 | 117.5–118.2 |
| I | phthalimido | benzyl | 93:7 | 82 (56) | 167.8–168.5 |
| I | phthalimido | DMB[3] | 94:6 | 85 (61) | 102.6–104.2 |
| I | Ox[4] | DMB | 91:9 | 84 | oil |
| I | CbzNH | DMB | >92:8 | 60 | 164.4–166 |
| I | phthalimido | —CH₂CO₂t-C₄H₉— | 91:9 | 65 (51) | 168.8–169.5 |
| I | phthalimido | —CH₂(CH₃)C=CH₂ | 92:8 | 74 | oil |
| I | phthalimido | 4-methoxyphenyl | 87:13 | 66 | 118.4–119.8 |

[1]Ratio of diastereomers determined either by 1H NMR spectroscopy or HPLC.
[2]Yields of chromatographed product as a mixture of diastereomers. Numbers in parentheses refer to yields of Ia or IIa after either crystallization or chromatography.
[3]2,4-dimethoxybenzyl.
[4]4,5-diphenyloxazolin-2-one-3-yl.

The preferred diastereoisomer is the natural isomer as shown by the above structural formula.

Examples of cis-azetidinones provided by the process of this invention are listed below wherein the headings have reference to formula 1 and R is a protected amino group.

| R | $R_1$ | $R_2$ | $R_3$ |
|---|---|---|---|
| Phthalimido | $CH_3$ | $CH_3$ | benzyl |
| Cbz amino[1] | $CH_3$ | $CH_3$ | 4-methoxybenzyl |
| Phthalimido | $C_6H_5$ | H | benzyl |
| Phthalimido | $C_6H_5$ | H | 2,4-dimethoxybenzyl |
| Phthalimido | $C_6H_5$ | H | 2-methyl-2-propenyl |
| Phthalimido | $C_6H_5$ | H | t-butoxycarbonyl-methyl |
| Cbz amino | $C_6H_5$ | H | 4-methoxybenzyl |
| Ox[2] | $C_6H_5$ | H | 2,4-dimethoxybenzyl |
| t-BOC amino[3] | $CH_3$ | $C_2H_5$ | 4-methoxyphenyl |
| Ox | 2-thienyl | H | benzyl |
| Phthalimido | 2-furyl | H | benzyl |
| Cbz | 4-chlorophenyl | H | 4-methoxybenzyl |
| t-BOC amino | —COO benzyl | H | —$CH_2$COO t-butyl |
| Cbz amino | —COOSi$(CH_3)_3$ | H | —$CH_2$COO benzyl |

[1]benzyloxycarbonylamino
[2]4,5-diphenyloxazolin-2-one-3-yl
[3]t-butyloxycarbonylamino Preferred azetidinones of the invention are represented by formula 1 wherein R is amino or protected amino and $R_1$ and $R_2$ independently are $C_1$-$C_6$ alkyl, especially methyl, phenyl, substituted phenyl or furyl, and $R_3$ is a nitrogen-protecting group. Other preferred azetidinones are represented when R is amino or protected amino and $R_3$ is a group of formula —CH($R_4$)COO$R_3'$.

The chiral azetidinones represented by formula 1 wherein R is an amino group are prepared by removal of the protecting group from the compound of formula 1 wherein R is an amino-protected group. For example, when R is a phthalimido group, the chiral 3β-phthalimido azetidinone is reacted with methyl hydrazine to effect removal of the phthaloyl group and provide the chiral 3β-amino azetidinone. Likewise, other amino-protecting groups, for example the Ox group and the Cbz group are removed by employing known hydrogenation conditions.

The 3-azidoazetidinones (formula 1, R=$N_3$) can be reduced, for example, by catalytic hydrogenation, to the 3-aminoazetidinone (formula 1, R=$NH_2$).

Because of the accessibility of the chiral 3β-amino azetidinones represented by formula 1 (R=$NH_2$), a further aspect of this invention provides chiral 3β-acylamino azetidinones represented by the following formula 2.

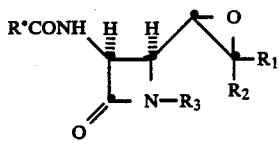

2

The acyl group $R^oCO$ of formula 2 is derived from a carboxylic acid and can be any of the acyl groups forming the 7-position side chain of a cephalosporin antibiotic or the 6-position side chain of a penicillin antibiotic.

Preferred compounds of the invention are represented by formula 2 where, in the 3-position acyl group $R^oC(O)$—, $R^o$ is hydrogen; $C_1$-$C_6$ alkyl, $C_1$-$C_6$ alkyl substituted by cyano, carboxy, halogen, amino, $C_1$-$C_4$ alkoxy, $C_1$-$C_4$ alkylthio, or trifluoromethylthio; a phenyl or substituted phenyl group represented by the formula

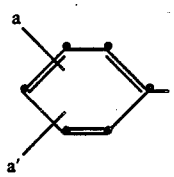

wherein a and a' independently are hydrogen, halogen, hydroxy, $C_1$-$C_4$ alkoxy, $C_1$-$C_4$ alkanoyloxy, $C_1$-$C_4$ alkyl, $C_1$-$C_4$ alkylthio, amino, $C_1$-$C_4$ alkanoylamino, $C_1$-$C_4$ alkylsulfonylamino, carboxy, carbamoyl, aminosulfonyl, hydroxymethyl, aminomethyl, or carboxymethyl;

a group represented by the formula

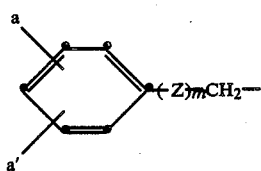

wherein a and a' have the same meanings as defined above, Z is O or S, and m is 0 or 1;

a heteroarylmethyl group represented by the formula $$R_6—CH_2—$$

wherein $R_6$ is thienyl, furyl, benzothienyl, benzofuryl, pyridyl, 4-pyridylthio pyrimidyl, pyridazinyl, indolyl, pyrazolyl, imidazolyl, triazolyl, tetrazolyl, oxazolyl, thiazolyl, oxadiazolyl, thiadiazo.yl-, and such heteroaryl groups substituted by amino, hydroxy, halogen, $C_1$-$C_4$ alkyl, $C_1$-$C_4$ alkoxy, $C_1$-$C_4$ alkylsulfonylamino;

a substituted methyl group represented by the formula

wherein $R_7$ is cyclohex-1,4-dienyl, or a phenyl group or substituted phenyl group represented by the formula

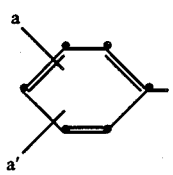

wherein a and a' have the above defined meanings, or $R_7$ is $R_6$ as defined above, and Q is hydroxy, $C_1$-$C_4$ alkanoyloxy, carboxy, sulfo, amino, or sulfoamino;
or R is a keto group or an oximino-substituted group represented by the formulae

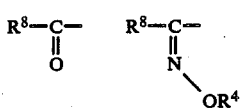

wherein R₈ is R₆ or R₇ as defined above and R₉ is hydrogen, C₁–C₄ alkyl, C₁–C₄ alkyl substituted by halogen or amino, a carboxy-substituted alkyl or cycloalkyl group represented by the formula

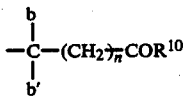

wherein b and b' independently are hydrogen, or C₁–C₃ alkyl, n is 0, 1, 2, or 3; and b and b' when taken together with the carbon to which they are bonded form a 3- to 6-membered carbocyclic ring, and R₁₀ is hydroxy, C₁–C₄ alkoxy, amino, C₁–C₄ alkylamino, or di(C₁–C₄ alkyl)amino;
or R₉ is a cyclic lactam represented by the formula

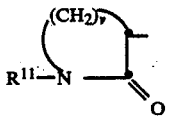

wherein v is 2, 3, or 4; and R₁₁ is hydrogen or C₁–C₃ alkyl;
or R₉ is a heteroarylmethyl group represented by the formula

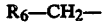

wherein R₆ has the same meanings as defined hereinabove.

In the above definition of the preferred compounds represented by formula 2, C₁–C₆ alkyl refers to the straight and branched chain alkyl groups such as methyl, ethyl, n-propyl, isopropyl, n-butyl, t-butyl, n-pentyl, n-hexyl, 3-methylpentyl, and like alkyl groups; C₁–C₆ alkyl substituted by cyano refers to cyanomethyl, cyanoethyl, 4-cyanobutyl, and the like; C₁–C₆ alkyl substituted by carboxy refers to such groups as carboxymethyl, 2-carboxyethyl, 2-carboxypropyl, 4-carboxybutyl, 5-carboxypentyl, and the like; C₁–C₆ alkyl substituted by halogen refers to chloromethyl, bromomethyl, 2-chloroethyl, 1-bromoethyl, 4-chlorobutyl, 4-bromopentyl, 6-chlorohexyl, 4-fluorobutyl, 3-fluoropropyl, fluoromethyl, and the like; C₁–C₆ alkyl substituted by amino refers to such groups as 2-aminoethyl, aminomethyl, 3-aminopropyl and 4-aminobutyl; C₁–C₆ alkyl substituted by C₁–C₄ alkoxy refers to methoxymethyl, 2-methoxyethyl, 2-ethoxyethyl, ethoxymethyl, 3-propoxypropyl, 3-ethoxybutyl, 4-t-butyloxybutyl, 3-methoxypentyl, 6-methoxyhexyl, and like groups; C₁–C₆ alkyl substituted by C₁–C₄-alkylthio refers to such groups as for example methylthiomethyl, 2-methylthioethyl, 2-ethylthiopropyl, 4-methylthiobutyl, 5-ethylthiohexyl, 3-t-butylthiopropyl, and like groups; C₁–C₆ alkyl substituted by trifluoromethyl is exemplified by 2,2,2-trifluoroethyl, 3,3,3-trifluoropropyl, 4,4,4-trifluorobutyl, and the like; and C₁–C₆ alkyl substituted by trifluoromethylthio refers to, for example, trifluoromethylthiomethyl, 2-(trifluoromethylthio)ethyl, 2-(trifluoromethylthio)propyl, 4-(trifluoromethylthio)butyl, 5-(trifluoromethylthio)hexyl, and like C₁–C₆ alkyl substituted groups.

When in formula 2 R° is a substituted phenyl group wherein the substituent(s) are represented by "a" and "a'", examples of such groups are halophenyl such as 4-chlorophenyl, 3-bromophenyl, 2-fluorophenyl, 2,4-dichlorophenyl, and 3,5-dichlorophenyl; hydroxyphenyl such as 2-hydroxyphenyl, 3-hydroxyphenyl, 4-hydroxyphenyl, 2,4-dihydroxyphenyl, and 3,4-dihydroxyphenyl; alkoxyphenyl, such as 2,6-dimethoxyphenyl, 4-methoxyphenyl, 3-ethoxyphenyl, 3,4-dimethoxyphenyl, 4-t-butyloxyphenyl, 4-methoxy-3-ethoxyphenyl, and 4-n-propoxyphenyl; alkanoyloxyphenyl such as 2-acetoxyphenyl, 4-propionoxyphenyl, 4-formyloxyphenyl, 4-acetoxyphenyl, 3-butyryloxyphenyl, and 3-acetoxyphenyl; alkylphenyl such as 4-methylphenyl, 2-methylphenyl, 2,4-dimethylphenyl, 3-t-butylphenyl, 4-ethylphenyl, 4-ethyl-3-methylphenyl, and 3,5-dimethylphenyl; alkylthiophenyl such as 4-methylthiophenyl, 3-n-butylthiophenyl, 2-ethylthiophenyl, 3,4-dimethylthiophenyl, and 3-n-propylthiophenyl; aminophenyl such as 2-aminophenyl, 4-aminophenyl, 3,5-diaminophenyl, and 3-aminophenyl; alkanoylamino such as 2-acetylamino, 4-acetylamino, 3-propionylamino, and 4-butyrylamino; alkylsulfonylaminophenyl such a 3-methylsulfonylaminophenyl, 4-methylsulfonylaminophenyl, 3,5-(dimethylsulfonylamino)phenyl, 4-n-butylsulfonylaminophenyl, and 3-ethylsulfonylaminophenyl; carboxyphenyl such as 2-, 3-, or 4-, carboxyphenyl, 3,4-dicarboxyphenyl, and 2,4-dicarboxyphenyl; carbamoylphenyl such as 2-carbamoylphenyl, 2,4-dicarbamoylphenyl, and 4-carbamoylphenyl; hydroxymethylphenyl such as 4-hydroxymethylphenyl and 2-hydroxymethylphenyl; aminomethylphenyl such as 2-aminomethylphenyl and 3-aminomethylphenyl; and carboxymethylphenyl such as 2-carboxymethylphenyl, 4-carboxymethylphenyl, and 3,4-dicarboxymethylphenyl; and the substituted phenyl groups bearing different substituents such as 4-chloro-3-methylphenyl, 4-fluoro-3-hydroxyphenyl, 3,5-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butyloxy-2-hydroxyphenyl, 4-acetylamino-3-methoxyphenyl, 3-amino-4-ethylphenyl, 2-aminomethyl-4-chlorophenyl, 2-hydroxymethyl-3-methoxyphenyl, 2-hydroxymethyl-4-fluorophenyl, 2-acetoxy-4-aminophenyl, 4-acetoxy-3-methoxyphenyl, 3-isopropylthio-4-chlorophenyl, 2-methylthio-4-hydroxymethylphenyl, 4-carboxy-3-hydroxyphenyl, 4-ethoxy-3-hydroxyphenyl, 4-methylsulfonylamino-2-carboxyphenyl, 4-amino-3-chlorophenyl, and 2-carboxymethyl-4-hydroxyphenyl.

Examples of R°CO— groups of formula 2 wherein R° is a group represented by the formula

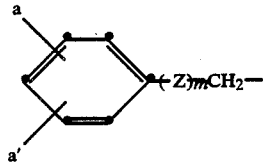

with m=0 are: phenylacetyl, 4-hydroxyphenylacetyl, 4-chlorophenylacetyl, 3,4-dichlorophenylacetyl, 4-methoxyphenylacetyl, 3-ethoxyphenylacetyl, 2-aminomethylphenylacetyl, 3-carboxyphenylacetyl, 4-acetoxyphenylacetyl, 3-aminophenylacetyl, and 4-acetylaminophenylacetyl; and with m=1 and Z=0, phenoxyacetyl, 4-chlorophenoxyacetyl, 4-fluorophenoxyacetyl, 3-aminophenoxyacetyl, 3-hydroxyphenoxyacetyl, 2-methoxyphenoxyacetyl, 2-methylthiophenoxyacetyl, 4-acetylaminophenoxyacetyl, 3,4- dimethylphenoxyacetyl, and 3-hydroxymethylphenoxyacetyl; and with m=1 and Z=S, phenylthioacetyl, 4-chlorophenylthioacetyl, 3,4-dichlorophenylthioacetyl, 2-fluorophenylthioacetyl, 3-hydroxyphenylthioacetyl, and 4-ethoxyphenylthioacetyl.

Examples of $R_6$—$CH_2CO$-groups of formula 2 wherein $R_6$ is a heteroaryl group are: 2-thienylacetyl, 3-thienylacetyl, 2-furylacetyl, 2-benzothienylacetyl, 2-benzofurylacetyl, 3-benzothienylacetyl, indol-2-ylacetyl, 1H-tetrazol-1-ylacetyl, oxazol-2-ylacetyl, oxazol-4-ylacetyl, thiazol-4-ylacetyl, 2-aminothiazol-4-ylacetyl, 1,3,4-oxadiazol-2-ylacetyl, 1,3,4-thiadiazol-2-ylacetyl, 5-ethyl-1,3,4-thiadiazol-2-ylacetyl, pyridyl-2-acetyl, pyridyl-3-acetyl, pyridyl-4-acetyl, 4-aminopyridyl-3-acetyl, pyrimidin-2-ylacetyl, pyrimidin-4-ylacetyl, 2-aminopyrimidin-4-ylacetyl, 4-aminopyrimidin-2-ylacetyl, pyridazin-3-acetyl, pyridazin-4-acetyl, pyrazol-3-ylacetyl, 3-methylpyrazol-1-ylacetyl, imidazol-2-ylacetyl, imidazol-1-ylacetyl, 2-aminoimidazol-3-ylacetyl, 3-chloroimidazol-4-ylacetyl, and like heteroaryl groups optionally substituted by amino, $C_1$–$C_4$ alkylsulfonylamino, hydroxy, halo, $C_1$–$C_4$ alkyl or $C_1$–$C_4$-alkoxy groups.

Examples of $R^oCO$— groups of formula 2 compounds wherein $R^o$ is a substituted methyl group represented by the formula $R_7$—CH(Q)— and Q is amino, carboxy, hydroxy, or sulfo, are 2-carboxy-2-phenylacetyl, 2-carboxy-2-(4-hydroxyphenyl)acetyl, 2-amino-2-phenylacetyl, 2-amino-2-(4-hydroxyphenyl)acetyl, 2-amino-2-(3-chloro-4-hydroxyphenyl)acetyl, 2-amino-2-(cyclohex-1,4-dien-1-yl)acetyl, 2-hydroxy-2-phenylacetyl, 2-formyloxy-2-phenylacetyl, 2-sulfo-2-phenylacetyl, 2-sulfo-2-(4-methylphenyl)acetyl, and 2-acetoxy-2-(3-hydroxyphenyl)acetyl, 2-amino-2-(2-thienyl)acetyl, 2-sulfoamino-2-phenylacetyl, 2-sulfoamino-2-(4-hydroxyphenyl)acetyl, 2-sulfoamino-2-(2-aminothiazol-4-yl)acetyl, 2-amino-2-(benzothien-2-yl)acetyl, 2-amino-2-(3-methylsulfonylphenyl)acetyl, 2-sulfoamino-2-(1,4-cyclohexadien)acetyl, 2-amino-2-(3-benzothienyl)acetyl, 2-amino-2-(1H-tetrazol-1-yl)acetyl, 2-hydroxy-2-(1,3,4-thiadiazol-2-yl)acetyl, 2-amino-2-(2-aminothiazol-4-yl)acetyl, 2-carboxy-2-(2-thienyl)acetyl, 2-carboxy-2-(benzothien-2-yl)acetyl, and 2-hydroxy-2-(benzofur-2-yl)acetyl.

Examples of $R^oCO$ acyl groups of the compounds represented by formula 2 when $R^o$ is a keto group or an oximino-substituted group represented by the formulae

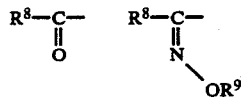

are the keto groups 2-oxo-2-phenylacetyl, 2-oxo-2-(2-thienyl)acetyl, 2-oxo-2-(2-aminothiazol-4-yl)acetyl; and oximino-substituted groups 2-phenyl-2-methoxyiminoacetyl, 2-(2-thienyl)-2-ethoxyiminoacetyl, 2-(2-furyl)-2-methoxyiminoacetyl, 2-(2-benzothienyl)-2-carboxymethoxyiminoacetyl, 2-(2-thienyl)-2-(2-carboxyethoxy)iminoacetyl, 2-(2-amino-1,2,4-thiadiazol-4-yl)-2-methoxyiminoacetyl, 2-(2-aminothiazol-4-yl)-2-methoxyiminoacetyl, 2-(2-chlorothiazol-4-yl)-2-methoxyiminoacetyl, 2-(2-aminothiazol-4-yl)-2-(2-carboxyprop-2-yl)oxyiminoacetyl, 2-(2-aminothiazol-4-yl)-2-(2-carbamoylprop-2-yl)oxyiminoacetyl, 2-(5-amino-1,3,4-thiadiazol-2-yl)-2-methoxyiminoacetyl, 2-(2-aminothiazol-4-yl)-2-(pyrrolidin-2-one-yl)oxyiminoacetyl, 2-(2-aminothiazol-4-yl)-2-(1-methylpyrrolidin-2-one-3-yl)oxyiminoacetyl, 2-phenyl-2-(pyrrolidin-2-one-3-yl)oxyiminoacetyl, 2-(2-aminooxazol-4-yl)-2-(1-ethylpyrrolidin-2-one-3-yl)oxyiminoacetyl, 2-(2-aminothiazol-4-yl)-2-(1-ethylpiperidin-2-one-3-yl)-2-oxyiminoacetyl, and 2-(2-furyl)-2-(pyrrolidin-2-one-3-yl)oxyiminoacetyl.

Preferred 3β-acylazetidinones are represented by formula 2 wherein $R^oCO$ is phenylacetyl or phenoxyacetyl optionally substituted.

The 3-acylamino compounds represented by formula 2 are prepared by conventional acylation of the 3β-amino azetidinone (formula 1, R=NH_2). For example, the carboxylic acid $R^oCOOH$ forming the acyl group $R^oCO$ is converted to an active derivative such as an acid halide, an acid azide, an anhydride or an active ester which is used for the acylation of the amino nucleus compound. For example, phenoxyacetic acid is converted to phenoxyacetyl chloride and is added to a solution of 3β-amino azetidinone oxide in an inert solvent containing an acid scavenger, for example sodium carbonate or a tertiary amine such as triethylamine. The N-acylation can be carried out by the procedures commonly employed in the β-lactam art for the preparation of 6-acylamino penicillins with the penicillin nucleus (6-APA) or 7-acylamino cephalosporins with the cephalosporin nuclei, for example 7-ACA or 7-ADCA. The customary precautions employed in the acylation should be observed, for example any free amino or carboxy groups present either in the acid moiety or the 3-amino azetidinone epoxide, are protected with conventional protecting groups during the acylation.

The chiral epoxy azetidinones represented by formula 1 which have the natural chirality are useful intermediates for the preparation of antibiotic substances. For this purpose, the epoxy group of 1 is cleaved by treatment with periodic acid to provide the corresponding chiral 4-formyl azetidinone. The latter can be reduced, for example with sodium cyanoborohydride, to provide the corresponding chiral 4-hydroxymethyl azetidinone. The 4-hydroxymethyl compound can be converted to the isocephalosporins described in *J. Am. Chem. Soc.*, 99, 2353–2355 (1977). The 4-hydroxymethylazetidinone can be converted to the monocyclic antibiotic known as AMA 1080, 3β-[2-(2-aminothiazol-4-yl)-2-(Z)-carboxymethoxyiminoacetamido]-4-carbamoyloxymethyl-2-azetidinone-1-sulfonate, Chung-Chen Wei, et al., *23rd Interscience Conference on Antimicrobial Agents and Chemotherapy*, 1983, Abstract No. 324.

The 4-hydroxymethyl derivative also can be used to prepare the O-2-isocephem antibiotics as described in Mastalerz, et al., *Chem. Commun* 1987, 1283–1284, and the penicillin nuclear analogs, the 7-oxo-1,3-diazabicyclo[3.2.0]heptane-2-carboxylic acids described in Huffman, W. F., et al., *J. Am. Chem. Soc.*, 1977, 99:7, 2352–2353. In addition, the azetidinones represented by formula 1 can be used to prepare 1-carbapenems and 1-carbacephems.

The 3β-acylamino chiral epoxide azetidinones represented by formula 2 can likewise be converted by known methods to antibiotic substances. In this instance, however, one may acylate the 3β-amino azetidinone represented by formula 1 with the desired acyl moiety prior to conversion to the desired product. For example, one can acylate the chiral 3β-amino epoxy azetidinone with phenylacetyl chloride to obtain the 3β-phenylacetylamino chiral azetidinone, and thereafter carry out the epoxide cleavage to provide the corresponding 4-formyl azetidinone. The latter can be converted, for example as described above, to the desired antibiotic having the desired side chain.

The following examples are provided to further illustrate the invention and are not to be considered as limiting thereof.

In the following examples, analytical thin layer chromatography (TLC) was performed using EM Reagents 0.25 mm silica gel 60-F plates. Melting points were determined with a Buchi SMP-20 melting point apparatus equipped with an Omega Model 450 AET thermocouple thermometer and are uncorrected. Infrared spectra (IR) were recorded on a Perkin Elmer 781 spectrophotometer. $^1$H NMR spectra were recorded on Bruker AM-250 (250 MHz) and AM-500 (500 MHz) spectrometers. Data are reported as follows: chemical shift from internal tetramethylsilane on the δ scale, multiplicity (s=singlet, d=double, t=triplet, m=multiplet, and br=broad), integration, coupling constant (Hz), and interpretation. $^{13}$C spectra were recorded on a Bruker AM-250 (62.5 MHz) spectrometer. Chemical shifts are reported in ppm on the δ scale as referenced to deuterochloroform (77.0 ppm). All spectra were recorded with complete proton decoupling. Optical rotations were determined on a Jasco DIP-181 digital polarimeter at the indicated wavelength and are reported as follows: [α]$_{wavelength}$ (concentration c in g/100 mL, solvent). Analytical high pressure chromatography (HPLC) was performed on a Hewlett Packard HP1090 Chromatograph equipped with a diode array UV detector using a DuPont Zorbax Sil column (4.6 mm×25 cm, 5 μm silica gel) or a 5 μm Vydac 15% bonded C$_{18}$ (reverse phase) column as indicated. HPLC data is reported as follows: (column, eluant composition, flow rate, detector wavelength). Preparative liquid chromatography was performed using a forced flow (flash chromatography) of the indicated solvent system on EM Reagents silica gel 60 (230–400 mesh).

Combustion analyses were performed by Spang Microanalytical Laboratory (Eagle Harbor, Mich.).

Air and moisture-sensitive reactions were carried out in flame-dried glassware under an atmosphere of dry nitrogen. When necessary, solvents and reagents were dried and distilled under nitrogen prior to use. Dichloromethane and triethylamine were distilled from calcium hydride. Toluene was distilled from sodium metal. Tetrahydrofuran and diethyl ether were distilled from sodium benzophenone ketyl. Dimethyl sulfoxide was distilled under reduced pressure from calcium hydride and stored over activated 4 Å molecular sieves under an argon atmosphere. Reagent grade anhydrous dimethylformamide was stored over activated 4 Å molecular sieves under argon CrO$_3$ was dried at 100° C. and 0.1 mm Hg over P$_2$O$_5$. 4 Å molecular sieves were activated at 400° C. prior to use. All other reagents and solvents were used as received Preparation of Chiral Epoxy Alcohols The epoxy alcohols were prepared in accordance with the general procedures described in Sharpless, et al., *J. Am. Chem. Soc.*, 1987, 109, 5765–5780, and as illustrated below for two such epoxy alcohols.

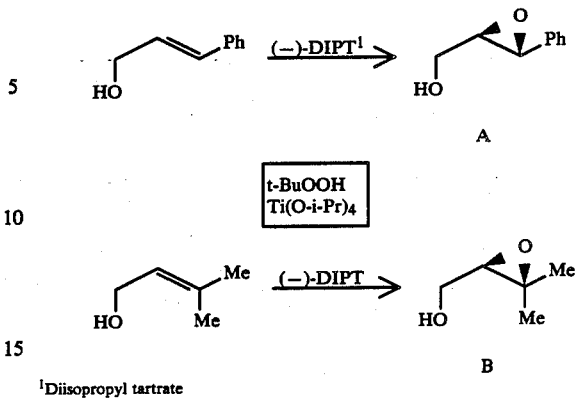

[1]Diisopropyl tartrate

For the epoxy alcohols whose absolute stereochemistry is illustrated above, the (−)-diisopropyl tartrate catalyst is required as proscribed in the cited Sharpless publication. In the expoxidation to give epoxide A, the asymmetric induction exceeds 98%, while the epoxidation to give B was somewhat less stereoselective (93% ee).

Preparation of Chiral Epoxy Aldehydes (1) (R)-2-Formyl-3,3-dimethyloxirane

In a flame-dried 25 mL flask under nitrogen, oxalyl chloride (0.10 mL, 1.2 mmol) was dissolved in 4.0 mL of anhydrous dichloromethane, and the resulting solution was cooled to −78° C. A cold (−78° C.) solution of dimethylsulfoxide (0.17 mL, 2.4 mmol) in 2.0 mL of dichloromethane was added dropwise via cannula such that the temperature did not rise about −60° C. After 3 minutes, a cold (−78° C.) solution of (S)-2-hydroxymethyl-3,3-dimethyloxirane (109 mg, 1.07 mmol, 90% optical purity) in 1.0 mL of dichloromethane was added with washing of any residual alcohol into the reaction with two 1.0 mL portions of dichloromethane. The solution was stirred for 15 minutes producing a white precipitate before triethylamine (0.75 mL, 5.4 mmol) was added. The solution cleared, then became cloudy.

The reaction temperature was maintained at −78° C. for 1 hour before allowing the reaction to warm to 0° C. over a period of 30 minutes. The mixture was poured into 50 mL of pentane and filtered through silica gel (4×8 cm, eluting with 100 mL of pentane, 100 mL of 50% diethyl ether in pentane, and 100 mL of diethyl ether, collecting 100 mL fractions). The fractions containing the desired material (TLC) were combined and concentrated to ca. 5 mL at atmospheric pressure while maintaining the distillation temperature below 40° C. This solution was used for imine formation without further purification.

(2) (2R,3S)-2-Formyl-3-phenyloxirane

In a flame-dried 25 mL flask under nitrogen, oxalyl chloride (0.22 mL, 2.44 mmol) was dissolved in 5.0 mL of anhydrous dichloromethane and the resulting solution was cooled to −78° C. A cold (−78° C.) solution of dimethylsulfoxide (0.35 mL, 4.87 mmol) in 1.0 mL of dichloromethane was added dropwise via cannula such that the temperature did not rise above −60° C. After 3 minutes, a cold (−78° C.) solution of (2S,3S)-2-hydroxymethyl-3-phenyloxirane (203 mg, 1.35 mmol, >98% optical purity) in 1.0 mL of dichloromethane was added with washing of any residual alcohol into the reaction with two 1.0 mL portions of dichloromethane. The solution was stirred for 15 minutes producing a white precipitate before triethylamine (1.55 mL, 11.1 mmol) was added. The solution cleared, then became cloudy. The reaction temperature was maintained at $-78°$ C. for 1 hour before allowing the reaction to warm to $0°$ C. over a period of 30 minutes. The mixture was partitioned between 50 mL each of dichloromethane and water. The aqueous phase was extracted with two 50 mL portions of dichloromethane. The combined organic solutions were washed with saturated aqueous sodium chloride, filtered through cotton, and concentrated under reduced pressure at room temperature. The residual yellow oil was flash chromatographed (3×12 cm siliga gel, 40% diethyl ether in pentane) to provide 159 mg (79%) of a yellow oil: $R_f$ 0.51 (50:50 ethyl acetate/hexane) IR (CHCl$_3$) 3020, 1740 cm$^{-1}$; $^1$H NMR (CDCl$_3$, 250 MHz) δ 9.20 (d, 1H, J=6.1 Hz, CHO), 7.47–7.24 (5H, ArH), 4.18 (d, 1H, J=1.8 Hz, oxirane CHCHPh), 3.45 (dd, 1H, J=1.8, 6.1 Hz, oxirane CHCHPh).

(3) The (2R,3S)-2-formyl-3-phenyloxirane obtained in Preparation 2 was also obtained via oxidation with pyridine-sulfur trioxide as follows:

To a stirred mixture of (2S,3S)-2-hydroxymethyl-3-phenyloxirane (201 mg, 1.34 mmol), triethylamine (1.23 mL, 8.84 mmol), and 1.2 mL of dimethylsulfoxide in a 25 mL flame-dried flask at room temperature under nitrogen was added a solution of sulfur trioxide-pyridine (639 mg, 4.02 mmol) in 24 mL of dimethylsulfoxide. The rate of addition was controlled to maintain the temperature of the reaction below $28°$ C. as monitored with an internal thermocouple probe. After 10 minutes, the mixture was partitioned between 200 mL of diethyl ether/hexanes and 50 mL of water. The organic solution was extracted with two 25 mL portions of water, and 10 mL each of 0.5M cupric sulfate and saturated aqueous sodium chloride. The solution was dried over magnesium sulfate and concentrated to afford a colorless oil which was chromatographed (5×10 cm silica gel, 40:60 diethyl ether/pentane, 50 mL fractions) to provide 136 mg (69%) of the desired aldehyde.

(4) The (2R,3S)-2-formyl-3-phenyloxirane was also prepared via CrO$_3$-pyridine oxidation as follows.

To a mixture of chromium trioxide (5.99g, 59.9 mmol), celite (2.3 g), crushed 4 Å molecular sieves (2.3 g, activated), and anhydrous dichloromethane (120 mL) in a flame-dried 250 mL flask under nitrogen was added pyridine (9.7 mL, 120 mmol). The mixture was stirred for 15 minutes before adding via cannula a solution of (2S,3S)-2-hydroxymethyl-3-phenyloxirane (1.50 g, 9.99 mmol), in 5.0 mL of dichloromethane, washing any residual alcohol into the reaction with two 2.0 mL portions of dichloromethane. After 15 minutes, the mixture was poured into 600 mL of anhydrous diethyl ether, and the result was filtered through a 5 cm pad of florisil in a 150 mL fritted glass funnel. The removal of solvents under reduced pressure afforded a yellow oil which was chromatographed (5×12 cm silica gel, 40:60 diethyl ether/pentane, 25 mL fractions). The desired aldehyde was obtained as a nearly colorless oil (677 mg, 46%) which became a waxy solid upon cooling to $-20°$ C.

Representative Procedure for Epoxyimine Formation (5) (2S,3S)-2-[N-(2,4-Dimethoxybenzyl)formimino]-3-phenyloxirane To a solution of (2S,3S)-2-formyl-3-phenyloxirane (430 mg, 2.90 mmol) in 8.0 mL of dichloromethane under nitrogen was added a solution of 2,4-dimethoxybenzylamine (461 mg, 2.75 mmol) in 1.0 mL of dichloromethane via cannula. Residual amine was washed into the reaction flask with 1.0 mL of dichloromethane. Molecular sieves (2.3 g of pellets, 4 Å, activated) were added and the mixture was allowed to stand for 12 hours. This solution was used directly in the cycloaddition after removing and concentrating a small aliquot for spectral analysis: IR (CHCl$_3$) 3016, 1615, 1510 cm$^{-1}$; $^1$H NMR (CDCl$_3$, 250 MHz) δ 7.40–7.24 (6H, N=CH, ArH), 7.14 (d, 1H, J=8.8 Hz, ArH), 6.52–6.43 (2H, ArH), 4.62 (s, 2H, NCH$_2$Ar), 3.69 (d, 1H, J=1.9 Hz, oxirane CHCHPh), 3.82 (s, 3H, OCH$_3$), 3.81 (s, 3H, OCH$_3$), 3.62 (dd, 1H, J=1.9, 7.0 Hz, oxirane CHCHPh).

EXAMPLE 1

[3R,4R,4(2S)]-1-Benzyl-3-phthalimido-4-(3,3-dimethyloxiran-2-yl)-2-azetidinone

Phthalimidoacetyl chloride (400 mg, 1.79 mmol) was placed in a flame-dried 25 mL flask, the system was purged with nitrogen, and the solid was dissolved in 5.0 mL of anhydrous dichloromethane. The resulting solution was cooled to $-78°$ C., and triethylamine (0.37 mL, 2.7 mmol) was added, producing an orange solution containing a flocculent white precipitate. After 15 minutes, a solution of the imine prepared from (R)-2-formyl-3,3-dimethyloxirane and benzylamine (1.79 mmol) in 4.0 mL of dichloromethane was added via cannula. Residual imine was washed into the reaction with 1.0 mL of dichloromethane. The reaction was allowed to warm to $0°$ C. over 20 minutes, and this temperature was maintained for 2.5 hours before the mixture was partitioned between 50 mL of dichloromethane and 25 mL of 0.5M aqueous tartaric acid. The layers were separated, and the organic phase was washed with saturated aqueous sodium bicarbonate and filtered through cotton Concentration under reduced pressure afforded 606 mg of a yellow glass. Analysis of the crude material by high field $^1$H NMR (500 MHz) revealed the presence of two diastereomeric β-lactams (97:3). The product was purified by flash chromatography (3×16 cm silica gel, 50:50 ethyl acetate/hexanes, 10 mL fractions) which provided 552 mg (84%) of a single β-lactam. The product was crystallized from ethyl acetate/hexanes (ca. 50:50) for analysis: $R_f$ 0.24 (50 50 ethyl acetate/hexanes); m.p. 117.5°–118.2° C.; IR (CHCl$_3$) 3020, 1762, 1724, 1388 cm$^{-1}$; $^1$H NMR (CDCl$_3$, 250 MHz): δ 7.96–7.75 (4H, phthalimido ArH), 7.50–7.30 (5H, ArH), 5.50 (d, 1H, J=5.4 Hz, C3-H), 4.77 (d, 1H, J=14.9 Hz, NCH-H), 4.46 (d, 1H, J=14.9 Hz, NCH-H), 3.65 (dd, 1H, J=5.4, 7.3 Hz, C4-H), 2.95 (d, 1H, J=7.3 Hz, oxirane H), 1.02 (s, 3H, CH$_3$), 0.93 (s, 3H, CH$_3$); $^{13}$C NMR (CDCl$_3$, 62.5 MHz): δ 166.81, 162.97, 134.84, 134.60, 131.36, 128.76, 128.59, 127.89, 123.67, 60.89, 59.45, 56.65, 55.85, 45.79, 24.27, 19.06; $[α]_{365}$ +261° (c 1.02, CH$_2$Cl$_2$).

Analysis Calculated for C$_{22}$H$_{20}$N$_2$O$_4$: Theory: C, 70.20; H, 5.36. Found: C, 70.16; H, 5.33.

Minor diastereomer: $R_f$ 0.22 (50:50 ethyl acetate/hexanes); $^1$H NMR (CDCl$_3$, 250 MHz) δ 7.90–7.70 (4H, phthalimido ArH), 7.50–7.20 (5H, ArH), 5.53 (d, 1H, J=5.0 Hz, C3-H), 4.86 (d, 1H, J=15.2 Hz, NCH-H), 4.25 (d, 1H, J=15.2 Hz, NCH-H), 3.63 (dd, 1H, J=5.2, 9.3 Hz, C4-H), 2.70 (d, 1H, J=9.3 Hz, oxirane H), 1.00 (s, 3H, CH$_3$), 0.76 (s, 3H, CH$_3$).

EXAMPLE 2A

[3R,4R,4(2S,3S)]-1-Benzyl-3-phthalimido-4-(3-phenyloxiran-2-yl)-2-azetidinone Phthalimidoacetyl chloride (158 mg, 0.706 mmol) was placed in a flame-dried 25 mL flask, the system was purged with nitrogen, and the solid was dissolved in 2.7 mL of anhydrous dichloromethane. The resulting solution was cooled to −78° C., and triethylamine (0.15 mL, 1.1 mmol) was added, producing an orange solution containing a flocculent white precipitate. After 15 minutes, a solution of the imine prepared from (2R,3S)-2-formyl-3-phenyloxirane and benzylamine (0.706 mmol) in 2.7 mL of dichloromethane was added via cannula. Residual imine was washed into the reaction with 1.0 mL of dichloromethane. The reaction was allowed to warm to 0° C. over 20 minutes, and this temperature was maintained for 2.5 hours before the mixture was partitioned between 50 mL of dichloromethane and 25 mL of 0.5M aqueous tartaric acid. The layers were separated, and the organic phase was washed with saturated aqueous sodium bicarbonate and filtered through cotton. Concentration under reduced pressure afforded a yellow glass. Analysis of the crude material by high field $^1$H NMR (500 MHz) revealed the presence of two diastereomeric β-lactams (93:7). This observation was confirmed by HPLC analysis (95:5): major isomer: $t_r$ 11.16 minutes; minor isomer: $t_r$ 13.27 minutes (Vydac, 40:60 water/methanol, 1.5 mL/min, 260 nm). The product was purified by chromatography (3×16 cm, silica gel, 10:90 acetonitrile/toluene, 10 mL fractions) which provided 245 mg (82%) of the β-lactam as a mixture of diastereomers. The major product was crystallized from ethyl acetate/hexanes (ca. 25 mL, 20:80) to afford 169 mg (56%) of diastereomerically pure material: $R_f$ 0.22 (50:50 ethyl acetate/hexanes); mp 168°–168.5° C.; IR (CHCl$_3$) 3020, 1768, 1726, 1389 cm$^{-1}$; $^1$H NMR (CDCl$_3$, 250 MHz) δ 7.71–7.60 (4H, phthalimido ArH), 7.48–7.14 (5H, ArH), 7.03–6.86 (3H, ArH), 7.78–7.70 (2H, ArH), 5.49 (d, 1H, J=5.3 Hz, C3-H), 4.66 (AB, 2H, J=14.9 Hz, $v_o$δ=47.5 Hz, NCH$_2$Ph), 3.62 (dd, 1H, J=5.3, 6.8 Hz, C4-H), 3.37 (d, 1H, J=2.1 Hz, oxirane CHCHPh), 3.08 (dd, 1H, J=2.1, 6.8 Hz, oxirane CHCHPh); $^{13}$C NMR (CDCl$_3$, 62.5 MHz) δ 166.85, 162.92, 134.91, 134.75, 134.17, 131.23, 128.79, 128.59, 128.01, 127.93, 124.68, 123.37, 60.74, 59.53, 56.27, 54.65, 45.96; [α]$_{365}$+168° (c 1.00, CH$_2$Cl$_2$).

Analysis Calculated for C$_{26}$H$_{20}$N$_2$H$_4$: Theory: C, 73.57; H, 4.75. Found: C, 73.25; H, 5.57.

Minor diastereomer: $^1$H NMR (CDCl$_3$, 250 MHz) δ 7.90–7.70 (4H, phthalimido ArH), 7.50–7.12 (8H, ArH), 7.04–6.95 (2H, ArH), 5.51 (d, 1H, J=5.3 Hz, C3-H), 4.60 (AB, 2H, J=14.9 Hz, $v_o$δ=48.1 Hz, NCH$_2$Ph), 3.75 (dd, 1H, J=5.2, 6.6 Hz, C4-H), 3.58 (d, 1H, J=1.9 Hz, oxirane CHCHPh), 3.03 (dd, 1H, J=1.9, 6.6 Hz, oxirane CHCHPh).

EXAMPLE 2B

[3S,4S,4(2R,3R)]-1-Benzyl-3-phthalimido-4-(3-phenyloxiran-2-yl)-2-azetidinone The azetidinone was prepared in an identical manner using the enantiomeric oxirane: m.p. 167.8°–168.5° C.; [α]$_{365}$−168° (c 1.00, CH$_2$Cl$_2$).

Analysis Calculated for C$_{26}$H$_{20}$N$_2$O$_4$: Theory: C, 73.57; H, 4.75. Found: C, 73.50; H, 5.33.

EXAMPLE 3A

[3R,4R,4(2S,3S)]-1-(2,4-Dimethoxybenzyl)-3-phthalimido-4-(3-phenyloxiran-2-yl)-2-azetidinone Phthalimidoacetyl chloride (1.17 g, 5.25 mmol) was placed in a flame-dried 50 mL flask, the system was purged with nitrogen, and the solid was dissolved in 25 mL of anhydrous dichloromethane. The solution was cooled to −78° C., and triethylamine (1.10 mL, 7.89 mmol) was added, producing an orange solution containing a flocculent white precipitate. After 15 minutes, a solution of the imine prepared from (2R,3S)-2-formyl-3-phenyloxirane (820 mg, 5.53 mmol) and 2,4-dimethoxybenzylamine (879 mg, 5.25 mmol) in 15 mL of dichloromethane was added via cannula Residual imine was washed into the reaction with 2 mL of dichloromethane. The reaction was allowed to warm to 0° C. over 20 minutes, and this temperature was maintained for 2.5 hours before the mixture was partitioned between 150 mL of dichloromethane and 50 mL of 0.5M aqueous tartaric acid. The layers were separated, and the organic phase was washed with saturated aqueous sodium bicarbonate and filtered through cotton. Concentration under reduced pressure afforded a yellow glass Analysis of the crude material by high field $^1$H NMR at 250 MHz revealed the presence of two diastereomeric β-lactams (93:7). The product was purified by flash chromatography (5×15 cm silica gel, 50:50 ethyl acetate/hexanes, 20 mL fractions) which provided 2.17 g (85%) as a mixture of diastereomeric cis β-lactams. The major product was crystallized from ethyl acetate/hexanes (ca. 120 mL, 50:50) to afford 945 mg of colorless crystals. A second crop was obtained similarly providing a total of 1.64 g (65%) of material which was >98% diastereomerically pure by $^1$H NMR (250 MHz): $R_f$ 0.18 (1% methanol in dichloromethane); m.p. 102.6°–104.2° C.; IR (CHCl$_3$) 3020, 1768, 1727, 1521, 1390 cm$^{-1}$; $^1$H NMR (CDCl$_3$, 250 MHz) δ 7.65 (4H, phthalimido ArH), 7.32 (d, 1H, J=8.8 Hz, ArH), 7.00–6.86 (3H, ArH, 6.76–6.68 (2H, ArH), 6.55–6.47 (2H, ArH), 4.93 (d, 1H, J=5.4 Hz, C3-H), 4.76 (d, 1H, J=4.5 Hz, CH-H), 4.46 (d, 1H, J=14.5 Hz, CH-H), 3.89 (s, 3H, OCH$_3$), 3.83 (s, 3H, OCH$_3$), 3.60 (dd, 1H, J=5.5, 6.8 Hz, C4-H), 3.32 (d, 1H, J=2.1 Hz, oxirane CHCHPh), 3.09 (dd, 1H, J=2.2, 6.8 Hz, oxirane CHCHPh); $^{13}$C NMR (CDCl$_3$, 62.5 MHz) δ 166.95, 158.66, 135.21, 134.14, 131.39, 128.02, 127.89, 124.71, 123.35, 115.39, 104.39, 98.58, 60.79, 59.95, 56.12, 55.51, 55.42, 54.48, 40.71; [α]$_{365}$+153° (c 1.46, CH$_2$Cl$_2$).

Analysis Calculated for C$_{28}$H$_{24}$N$_2$O$_6$: Theory: C, 69.42; H, 4.99. Found: C, 69.35; H, 4.86.

EXAMPLE 3B

[3S,4S,4(2R,3R)]-1-(2,4-dimethoxybenzyl)-3-phthalimido-(3-phenyloxiran-2-yl)-2-azetidinone The azetidinone was prepared in an identical manner using the enantiomeric oxirane: m.p. 102.6°–104.2° C.; [α]$_{365}$−150° (c 1.47, CH$_2$Cl$_2$).

EXAMPLE 4

[3S,4S,4(2R,3R)]-1-(4-methoxyphenyl)-3-phthalimido-4-(3-phenyloxiran-2-yl)-2-azetidinone Phthalimidoacetyl chloride (119 mg, 0.532 mmol) was placed in a flame-dried 25 mL flask, the system was purged with nitrogen, and the solid was dissolved in 2.5 mL of anhydrous dichloromethane. The resulting solution was cooled to −78° C., and triethylamine (0.15 mL, 1.1 mmol) was added, producing an orange solution containing a flocculent white precipitate. After 15 minutes, a solution of the imine prepared from (2S,3R)-2-formyl-3-phenyloxirane (83 mg, 0.56 mmol) and 4-methoxyaniline (66 mg, 0.54 mmol) in 2.5 mL of dichloromethane was added via cannula. Residual imine was washed into the reaction with 1.0 mL of dichloromethane. The reaction was allowed to warm to 0° C. over 20 minutes, and this temperature was maintained for 2.5 hours before the mixture was partitioned between 50 mL of dichloromethane and 25 mL of 0.5M aqueous tartaric acid. The layers were separated, and the organic phase was washed with saturated aqueous sodium bicarbonate and filtered through cotton. Concentration under reduced pressure afforded a yellow glass. Analysis of the crude material by high field $^1$H NMR at 250 MHz revealed the presence of two diastereomeric β-lactams (87:13). The product was purified by flash chromatography (3×12 cm silica gel, 50:50 ethyl acetate/hexanes, 10 mL fractions) which provided 156 mg (66%) as a mixture of diastereomeric cis β-lactams (90:10). Crystallization from ethyl acetate/hexanes afforded an initial crop of feather-like crystals (30 mg) which proved to be a 50:50 mixture of diastereomeric cis β-lactams. The mother liquors produced colorless needles upon concentration (73 mg, 31%). This material proved to be the major diastereomer produced in the reaction and was >98% diastereomerically pure by $^1$H NMR (250 MHz): $R_f$ 0.35 (50:50 ethyl acetate/hexanes); m.p. 118.4°–119.8° C.; IR (CHCl$_3$) 3020, 1760, 1728, 1519, 1390, 1252 cm$^{-1}$; $^1$H NMR (CDCl$_3$, 250 MHz) δ 7.72–7.56 (4H, ArH), 7.04–6.87 (5H, ArH), 6.83–6.75 (2H, ArH), 5.67 (d, 1H, J=5.6 Hz, C3-H), 4.12 (dd, 1H, J=5.6, 7.0 Hz; C4-H), 3.83 (s, 3H, OCH$_3$), 3.60 (d, 1H, J=2.2 Hz, oxirane CHCHPh), 3.30 (dd, 1H, J=2.0, 7.0 Hz, CHCHPh); $^{13}$C NMR (CDCl$_3$, 62.5 MHz) δ 166.88, 159.63, 156.75, 134.74, 134.27, 131.30, 128.09, 124.71, 123.47, 118.44, 114.69, 61.06, 59.83, 55.70, 55.58, 55.48; [α]$_{365}$ −210° (c 1.03, CH$_2$Cl$_2$).

Analysis Calculated for C$_{26}$H$_{20}$N$_2$O$_5$: Theory: C, 70.90; H, 4.58. Found: C, 70.83; H, 4.53.

Minor diastereomer: $R_f$ 0.35 (50:50 ethyl acetate/hexanes); $^1$H NMR (CDCl$_3$, 250 MHz) δ 7.91–7.82 (2H, ArH), 7.80–7.72 (2H, ArH), 7.55–7.46 (2H, ArH), 7.29–7.12 (6H, ArH), 6.96–6.88 (2H, ArH), 5.67 (d, 1H, J=5.5 Hz, C3-H), 4.39 (dd, 1H, J=5.5, 5.96 Hz, C4-H), 3.96 (d, 1H, J=1.9 Hz, oxirane CHCHPh), 3.80 (s, 3H, OCH$_3$), 3.30 (dd, 1H, J=1.9, 5.5 Hz, CHCHPh).

EXAMPLE 5

[3S,4S,4(2R,3R)]-1-(2-Methyl-1-propenyl)-3-phthalimido-4-(3-phenyloxiran-2-yl)-2-azetidinone Phthalimidoacetyl chloride (112 mg, 0.501 mmol) was placed in a flame-dried 25 mL flask, the system was purged with nitrogen, and the solid was dissolved in 2.5 mL of anhydrous dichloromethane. The resulting solution was cooled to −78° C., and triethylamine (0.10 mL, 0.75 mmol) was added, producing an orange solution containing a flocculent white precipitate. After 15 minutes, a solution of the imine prepared from (2S,3R)-2-formyl-3-phenyloxirane (65 mg, 0.53 mmol) methallylamine hydrochloride (54 mg, 0.50 mmol), and triethylamine (0.07 mL, 0.50 mmol) in 2.5 mL of dichloromethane was added via cannula Residual imine was washed into the reaction with 1 mL of dichloromethane. The reaction was allowed to warm to 0° C. over 20 minutes, and this temperature was maintained for 2.5 hours before the mixture was partitioned between 50 mL of dichloromethane and 25 mL of 0.5M aqueous tartaric acid. The layers were separated, and the organic phase was washed with saturated aqueous sodium bicarbonate and filtered through cotton. Concentration under reduced pressure afforded a yellow oil. Analysis of the crude material by high field $^1$H NMR at 250 MHz revealed the presence of two diastereomeric β-lactams (92:8). The product was purified by flash chromatography (3×12 cm silica gel, 10:90 acetonitrile/toluene, 10 mL fractions) which provided 171 mg (88%) as a mixture of diastereomeric cis β-lactams which resisted all attempts at crystallization and resolution by chromatography. Major diastereomer: $R_f$ 0.31 (50:50 ethyl acetate/hexanes), 0.27 (10:90 acetonitrile/toluene); IR (CHCl$_3$) 3020, 1728, 1390, 1120, 900 cm$^{-1}$; $^1$H NMR (CDCl$_3$, 250 MHz) δ 7.72–7.59 (4H, phthalimido ArH), 7.05–6.90 (3H, ArH), 6.86–6.75 (2H, ArH), 5.56 (d, 1H, J=5.2 Hz, C3-H), 5.13 (br s, 1H, vinyl H), 5.06 (br s, 1H, vinyl H), 4.04 (br s, 2H, NCH$_2$), 3.72 (dd, 1H, J=5.2, 5.6 Hz, C4-H), 3.47 (d, 1H, J=2.1 Hz, oxirane CHCHPh), 3.20 (dd, 1H, oxirane CHCHPh), 1.90 (br s, 3H, CH$_3$).

Analysis Calculated for C$_{23}$H$_{20}$N$_2$O$_4$: Theory: C, 71.12; H, 5.19. Found: C, 70.93; H, 5.11

Minor diastereomer (partial data): $R_f$ 0.31 (50:50 ethyl acetate/hexanes), 0.27 (10:90 acetonitrile/toluene); $^1$H NMR (CDCl$_3$, 250 MHz) δ 7.91–7.70 (4H, phthalimido ArH), 4.99 (br s, 1H, vinyl H), 4.91 (br s, 1H, vinyl H), 4.04 (br s, 2H, NCH$_2$), 3.81 (dd, 1H, J=5.2, 5.6 Hz, C4-H), 1.78 (br s, 3H, CH$_3$).

EXAMPLE 6

[3S,4S,4(2R,3R)]-1-(tert-Butyloxycarbonylmethyl)-3-phthalimido-4-(3-phenyloxiran-2-yl)-2-azetidinone Phthalimidoacetyl chloride (151 mg, 0.674 mmol) was placed in a flame-dried 25 mL flask, the system was purged with nitrogen, and the solid was dissolved in 2.5 mL of anhydrous dichloromethane. The resulting solution was cooled to −78° C., and triethylamine (0.14 mL, 1.0 mmol) was added, producing an orange solution containing a flocculent white precipitate. After 15 minutes, a solution of the imine prepared from (2S,3R)-2-formyl-3-phenyloxirane (87 mg, 0.71 mmol) and tert-butylglycine (88 mg, 0.67 mmol) in 2.5 mL of dichloromethane was added via cannula. Residual imine was washed into the reaction mixture with 1 mL of dichloromethane. The reaction mixture was allowed to warm to 0° C. over 20 minutes, and this temperature was maintained for 2.5 hours before the mixture was partitioned between 50 mL of dichloromethane and 25 mL of 0.5M aqueous tartaric acid. The layers were separated, and the organic phase was washed with saturated aqueous sodium bicarbonate and filtered through cotton. Concentration under reduced pressure afforded a yellow glass. Analysis of the crude material by high field $^1$H NMR at 250 MHz revealed the presence of two diastereomeric β-lactams (91:9). The product was purified by flash chromatography (4×15 cm silica gel, 50:50 ethyl acetate/hexanes, 10 mL fractions) which provided 189 mg (65%) as a mixture of diastereomeric cis β-lactams. The major product was crystallized from ethyl acetate/hexanes affording 150 mg (51%) of colorless needles which proved to be >98% diastereomerically pure by $^1$H NMR (250 MHz): $R_f$ 0.36 (50:50 ethyl acetate/hexanes); m.p. 168.8°–169.5° C.; IR (CHCl$_3$) 3020, 1775, 1729, 1390, 1155 cm$^{-1}$; $^1$H NMR (CDCl$_3$, 250 MHz) δ 7.74–7.64 (4H, phthalimido ArH), 7.10–6.93 (5H, ArH), 5.64 (d, 1H, J=5.5 Hz, C3-H), 4.39 (d, 1H, J=17.9 Hz, NCH-H), 3.97 (d, 1H, J=17.9 Hz, NCH-H), 3.97 (dd, 1H, J=5.6, 7.4 Hz, C4-H), 3.49 (d, 1H, J=2.2 Hz, oxirane CHCHPh), 3.29 (dd, 1H, J=2.2, 7.5 Hz, oxirane CHCHPh); $^{13}$C NMR (CDCl$_3$, 62.5 MHz) δ 166.79, 166.34, 163.80, 134.82, 13.23, 131.09, 128.02, 124.75, 123.40, 2.85, 61.53, 59.63, 56.48, 54.63, 43.57, 28.04; [α]$_{365}$ −26.4° (c 1.23, CH$_2$Cl$_2$).

Analysis Calculated for C$_{25}$H$_{24}$N$_2$O$_6$: Theory: C, 66.95; H, 5.39. Found: C, 67.08; H, 5.35.

Minor diastereomer (partial data): R$_f$ 0.36 (50:50 ethyl acetate/hexanes); $^1$H NMR (CDCl$_3$, 250 MHz) δ 4.38 (d, 1H, J=17.9 Hz, NCH-H), 3.79 (d, 1H, J=17.9 Hz, NCH-H), 3.12 (dd, 1H, J=2.2, 4.2 Hz, oxirane CHCHPh).

EXAMPLE 7

[3R,4R,4(2S,3S)]-1-(2,4-Dimeththoxybenzyl)-3-carbobenzyloxyamino-4-(3-phenyloxiran-2-yl)-2-azetidinone To a stirred suspension of carbobenzyloxyglycine (249 mg, 1.19 mmol) in 2.4 mL of dichloromethane at 10° C. was added dimethylformamide (11.0 mL, 0.143 mmol) and oxalyl chloride (0.114 mL, 1.31 mmol). The solid gradually dissolved, providing a clear colorless solution after one hour. The cooling bath was removed and the solution was concentrated to near dryness under aspiration, protecting the system from moisture with a calcium sulfate drying tube. The residue was diluted with 2.4 mL of dichloromethane and the result was cooled to 0° C. This solution was transferred via cannula to a flask containing a stirred solution of triethylamine and the imine prepared from 2,4-dimethoxybenzylamine (199 mg, 1.19 mmol) and (2R,3S)-2-formyl-3-phenyloxirane (185 mg, 1.25 mmol) in 2.4 mL of dichloromethane at −10° C. The reaction mixture gradually became cloudy and the temperature was maintained between −8° and −12° C. for 2 hours before quenching with 10 mL of water. The result was partitioned between 40 mL of dichloromethane and 10 mL of 0.5M aqueous tartaric acid. The dichloromethane solution was washed with 10 mL of saturated aqueous sodium bicarbonate, filtered through cotton, and concentrated. The residual solid was chromatographed (5×12 cm silica gel, 1 L of 50:50 ethyl acetate/hexanes, 10 mL fractions) to afford 351 mg (60%) of a colorless solid containing a single β-lactam product. Although several other β-lactam diastereomers were isolated in less pure form, analysis of $^1$H NMR of the crude product mixture indicates that these products account for less than 5% of the mixture. An analytical sample of the major diastereomer was obtained by crystallization from hot toluene: R$_f$ 0.24 (50% ethyl acetate/hexane); m.p. 164.4°–166.0° C.; IR (CHCl$_3$) 3418, 23014, 1758, 1734, 1508, 1220 cm$^{-1}$; $^1$H NMR (CDCl$_3$, 250 MHz) δ 7.37–7.12 (11H, ArH), 7.50–6.43 (2H, ArH), 5.42 (br d, 1H, J=7.6 Hz, NH), 5.08 (dd, 1H, J=7.6, 5.3 Hz, C3-H), 4.98 (AB, 2H, J=12.1 Hz, v$_o$δ=25.1 Hz, OCH$_2$Ph), 4.70 (d, 1H, J=14.5 Hz, NCH-H), 4.23 (d, 1H, J=14.5 Hz, NCH-H), 3.82 (s, 6H, 2 x OCH$_3$), 3.69 (d, 1H, J=1.8 Hz, oxirane CHCHPh), 3.61 (dd, 1H, J=5.3, 5.3 Hz, C4-H), 2.94 (dd, 1H, J=1.8, 5.3 Hz, oxirane CHCHPh); $^{13}$C NMR (CDCl$_3$, 62.5 MHz) δ 172.50, 165.59, 135.67. 131.30, 128.38, 128.09, 127.99, 125.48, 104.24, 98.55, 67.26, 60.46, 59.76, 59.1, 55.42, 40.84; [α]$_{365}$ +38.2° (c 1.24, CH$_2$Cl$_2$).

Analysis Calculated for C$_{28}$H$_{28}$N$_2$O$_6$: Theory: C, 68.84; H, 5.78. Found: C, 68.93; H, 5.67.

EXAMPLE 8

[3S,4S,4(2R,3R)]-1-(2,4-Dimethoxybenzyl)-3-(3,4-diphenyl-2-oxazolonyl)-4-(3-phenyloxiran-2-yl)-2-azetidinone To a suspension of 3,4-diphenyl-2-oxazolonylacetic acid (281 mg, 0.951 mmol) in 3.0 mL of dichloromethane was added oxalyl chloride (0.12 mL, 1.4 mmol) and 10 μL of anhydrous dimethylformamide. The reaction mixture was protected from atmospheric moisture with a CaSO$_4$ drying tube. After one hour the solid had dissolved, producing a clear yellow solution which was concentrated under reduced pressure. The residual oil was dissolved in 4.0 mL of anhydrous dichloromethane, and the solution was concentrated to provide a colorless solid which was dissolved in 3.0 mL of anhydrous dichloromethane. The result was placed under nitrogen, cooled to −78° C., and triethylamine (0.21 mL, 1.5 mmol) was added, producing a white precipitate. After 15 minutes, a solution of the imine prepared from (2S,3R)-2-formyl-3-phenyloxirane (148 mg, 1.0 mmol) and 2,4-dimethoxybenzylamine (159 mg, 0.95 mmol) in 2.5 mL of dichloromethane was added via cannula. Residual imine was washed into the reaction with 1 mL of dichloromethane. The reaction was allowed to warm to 0° C. over 20 minutes, and this temperature was maintained for 2.5 hours before the mixture was partitioned between 50 mL of dichloromethane and 25 mL of 0.5M aqueous tartaric acid. The layers were separated, and the organic phase was washed with saturated aqueous sodium bicarbonate and filtered through cotton. Concentration under reduced pressure afforded a yellow foam. Analysis of the crude material by high field $^1$H NMR at 250 MHz revealed the presence of two diastereomeric β-lactams (91:9). The product was purified by flash chromatography (4×12 cm silica gel, 10:90 acetonitrile/toluene, 10 mL fractions) which provided 460 mg (84%) as a mixture of diastereomeric cis β-lactams which resisted all attempts at crystallization and resolution by chromatography. Major diastereomer: R$_f$ 0.23 (50% ethyl acetate/hexanes); IR (CHCl$_3$) 3020, 1770, 1618, 1510, 1160 cm$^{-1}$; $^1$H NMR (CDCl$_3$, 250 MHz) δ 7.58–7.49 (3H, ArH), 7.40–7.42 (2H, ArH), 7.28–7.02 (11H, ArH), 6.49–6.40 (2H, ArH), 4.73 (d, 1H, J=5.1 Hz, C3-H), 4.71 (d, 1H, J=14.5 Hz, NCH-H), 4.37 (d, 1H, J=14.5 Hz, NCH-H), 3.83 (s, 3H, OCH$_3$), 3.80 (s, 3H, OCH$_3$), 3.50–3.42 (2H, oxirane CHCHPh, C4-H), 3.38 (dd, 1H, J=5.0, 5.1 Hz, oxirane CHCHPh).

Analysis Calculated for C$_{35}$H$_{30}$N$_2$O$_6$: Theory: C, 73.26; H, 5.26. Found: C, 72.98; H, 5.16.

General Procedure for Epoxide Cleavage

To a stirred solution of the oxirane in of 50:50 dichloromethane/diethyl ether (30 mL/mmol) was added solid periodic acid hydrate (1.2 equivalents). The system was flushed with nitrogen and sealed with a polyethylene cap. After 12 hours, the mixture was partitioned between 1.0M aqueous sodium thiosulfate (50 mL/mmol) and dichloromethane (200 mL/mmol). The aqueous phase was washed with two portions of dichloromethane (50 mL/mmol), and the combined dichloromethane solutions were washed with saturated aqueous sodium chloride, filtered through cotton, and concentrated under reduced pressure to afford a colorless oil which was chromatographed (gradient elution, 50:50 ethyl acetate/hexanes to ethyl acetate). Yields of purified aldehyde range from 73 to 78%).

The following 4-formylazetidinones were obtained by the above procedure.

EXAMPLE 9

(3R,4R)-1-Benzyl-3-phthalimido-4-formyl-2-azetidinone $R_f$ 0.11 (50:50 ethyl acetate/hexanes); IR (CHCl$_3$) 3020, 1763, 1725, 1393 cm$^{-1}$; $^1$H NMR (CDCl$_3$, 250 MHz) δ 9.45 (d, 1H, J=2.9 Hz, CHO), 7.89–7.70 (4H, phthalimido ArH), 7.45–7.25 (5H, ArH), 5.66 (d, 1H, J=6.0 Hz, C3-H), 4.69 (AB, 2H, J=14.9 Hz, v$_o$δ=42.9 Hz, NCH$_2$Ph), 4.25 (dd, 1H, J=2.6, 6.2 Hz, C4-H).

EXAMPLE 10

(3R,4R)-1-(2,4-Dimethoxybenzyl)-3-phthalimido-4-formyl-2-azetidinone $R_f$ 0.51 (ethyl acetate); $^1$H NMR (CDCl$_3$, 250 MHz) δ 9.56 (d, 1H, J=2.5 Hz, CHO), 8.89–7.70 (4H, phthalimido ArH), 7.27 (d, 1H, J=8.2 Hz, ArH), 6.55–6.44 (2H, ArH), 5.56 (d, 1H, J=5.4 Hz, C3-H), 4.63 (s, 2H, NCH$_2$Ar), 4.16 (dd, 1H, J=2.5, 5.4 Hz, C4-H), 3.82 (s, 3H, OCH$_3$), 3.79 (s, 3H, OCH$_3$).

EXAMPLE 11

(3R,4R)-1-Benzyl-3-phthalimido-4-dimethoxymethyl-2-azetidinone prepared from the aldehyde derived from [3R,4R,4(2S)]-1-benzyl-3-phthalimido-4-[2-(3-dimethyl)oxiranyl]-2-azetidinone To a stirred solution of (3R,4R)-1-benzyl-3-phthalimido-4-formyl-2-azetidinone (32 mg, 0.095 mmol) in 0.6 mL of 1:5 trimethylorthoformate/methanol was added 0.5 mg of p-toluenesulfonic acid monohydrate. The mixture was warmed to 50° C. for 3 hours and was then partitioned between 40 mL of dichloromethane and 10 mL of saturated aqueous sodium bicarbonate. The organic solution was filtered through cotton and concentrated, providing a colorless oil which was flash chromatographed (3×10 cm silica gel, 100 mL of 50:50 ethyl acetate/hexanes then 100 mL of 75:25 ethyl acetate/hexanes) to afford 26 (72%) of a colorless oil which solidified upon standing at −20° C. An analytical sample was obtained by crystallization from dichloromethane/petroleum ether: $R_f$ 0.22 (50:50 ethyl acetate/hexanes); m.p. 128.8°–129.6° C.; IR (CHCl$_3$) 3020, 1765, 1393 cm$^{-1}$; $^1$H NMR (CDCl$_3$, 250 MHz) δ 7.94–7.71 (4H, phthalimido ArH), 7.45–7.30 (5H, ArH), 5.40 (d, 1H, J=5.3 Hz, C3-H), 4.60 (d, 1H, J=8.1 Hz, CH(OCH$_3$)$_2$), 4.55 (AB, 2H, J=15.1 Hz, v$_o$δ=40.4 Hz, NCH$_2$Ph), 3.92 (dd, 1H, J=5.4, 8.2 Hz, C4-H), 3.08 (s, 3H, OCH$_3$), 3.62 (s, 3H, OCH$_3$); $^{13}$C NMR (CDCl$_3$, 62.5 MHz) δ 6 167.15, 163.94, 136.08, 134.24, 131.74, 128.64, 128.12, 127.52, 123.58, 102.67, 57.42, 54.98, 54.39, 51.91, 45.83; [α]$_{365}$+50.3° (c 0.59, CH$_2$Cl$_2$).

EXAMPLE 12

(3R,4R)-1-Benzyl-3-phthalimido-4-dimethoxymethyl-2-azetidinone prepared from the aldehyde derived from [3R,4R,4(2S,3S)]-1-benzyl-3-phthalimido-4-[2-(3-phenyl)oxiranyl]-2-azetidinone The methyl acetal was prepared in a strictly analogous fashion: [α]$_{365}$+53.8° (c 1.30, CH$_2$Cl$_2$).

EXAMPLE 13

3R,4R,4(2S,3S)]-1-(2,4-Dimethoxybenzyl)-3-carbobenzyloxyamino-4-(3-phenyloxiran-2-yl)-2-azetidinone

[3R,4R,4(2S,3S)]-1-(2,4-Dimethoxybenzyl)-3-phthalimido-4-(3-phenyloxiran-2-yl)-2-azetidinone (199 mg, 0.411 mmol) was dissolved in 5.0 mL of dichloromethane at ambient temperature under nitrogen, methylhydrazine (0.044 mL, 0.82 mmol) was added, and the system was sealed with a polyethylene cap. After 36 hours the solution was concentrated to dryness under reduced pressure, and the residual solid was stirred with 30 mL of diethyl ether, filtering to remove any undissolved material. The ether solution was concentrated to give a colorless oil which was dissolved in 4.0 mL of tetrahydrofuran A solution of sodium bicarbonate (1.38 mg, 1.64 mmol) in 4.0 mL of water and carboberzyloxy chloride (0.084 mL, 0.62 mmol) were added. After 30 minutes, the reaction was quenched with dilute aqueous ammonium hydroxide, and the result was extracted with three 15 mL portions of dichloromethane. The combined extracts were washed with saturated aqueous sodium chloride, filtered through cotton, and concentrated. The crude product was flash chromatographed (3×10 cm silica gel, 50:50 to 70:30 ethyl acetate/hexanes) to afford 175 mg (87%) of product which was identical to the major product derived from the ketene-imine cycloaddition employing carbobenzyloxyglycine: $R_f$ 0.24 (50% ethyl acetate/hexane); m.p. 164.4°–166.0° C.; IR (CHCl$_3$) 3418, 3014, 1758, 1734, 1508, 1220 cm$^{-1}$; $^1$H NMR (CDCl$_3$, 250 MHz) δ 7.37–7.12 (11H, ArH), 7.50–6.43 (2H, ArH) 5.42 (br d, 1H, J=7.6 Hz, NH), 5.08 (dd, 1H, J=7.6, 5.3 Hz, C3-H), 4.98 (AB, 2H, J=12.1 Hz, v$_o$δ=25.1 Hz, OCH$_2$Ph), 4.70 (d, 1H, J=14.5 Hz, NCH-H), 4.23 (d, 1H, J=14.5 Hz, NCH-H), 3.82 (s, 6H, 2×OCH$_3$), 3.69 (d, 1H, J=1.8 Hz, oxirane CHCHPh), 3.61 (dd, 1H, J=5.3, 5.3 Hz, C4-H), 2.94 (dd, 1H, J=1.8, 5.3 Hz, oxirane CHCHPh).

EXAMPLE 14

(3S,4S)-1-(2,4-Dimethoxybenzyl)-3-carbobenzyloxyamino-4-hydroxymethyl-2-azetidinone To a stirred solution of the (3S,4S)-1-(2,4-dimethoxybenzyl)-3-phthalimido-4-formyl-2-azetidinone (584 mg, 1.48 mmol) in 15 mL of 1:2 acetic acid/ethanol at ambient temperature under nitrogen was added solid sodium cyanoborohydride (3 mg, 1.48 mmol). After 30 minutes, the reaction was quenched with several drops of acetone, and the result was basified by the careful addition of saturated aqueous sodium bicarbonate until no further gas evolution was observed. The mixture was partitioned between 100 mL each of dichloromethane and water, and the aqueous layer was extracted with two 20 mL portions of dichloromethane. The combined organic solutions were washed with 50 mL of saturated sodium chloride, filtered through cotton, and concentrated to afford 560 mg (95%) of a white foam which was used without further purification. A portion of this material (225 mg, 0.57 mmol) was dissolved in 20 mL of dichloromethane at ambient temperature under nitrogen, methylhydrazine (0.15 mL, 2.8 mmol) was added, and the system was sealed with a polyethylene cap. After 12 hours a white precipitate had formed. The mixture was diluted with 50 mL of diethyl ether and filtered through a fine glass fritted funnel. The clear colorless solution was concentrated to give an oil which was dissolved in 10 mL of 50:50 tetrahydrofuran/water.

Solid sodium bicarbonate (191 mg, 2.3 mmol) and carbobenzyloxy chloride (0.12 mL, 0.85 mmol) were added. After 30 minutes, the reaction was quenched with dilute aqueous ammonium hydroxide, and the result was extracted with three 50 mL portions of dichloromethane. The combined extracts were washed with saturated aqueous sodium chloride, filtered through cotton, and concentrated. The crude product was chromatographed (4×12 cm silica gel, 50:50 to 70:30 ethyl acetate/hexanes) to afford 189 mg (86% for two steps) of the desired material: $R_f$ 0.44 (ethyl acetate); m.p. 135.8°-136.4° C.; IR (CHCl$_3$) 3450 (broad), 3430, 3018, 2945, 1752, 1720, 1618, 1510, 1470, 1295, 1220, 1160, 1045 cm$^{-1}$; $^1$H NMR (CDCl$_3$, 250 MHz) δ 7.41–7.25 (5H, ArH), 7.19 (d, 1H, J=8.9 Hz, ArH), 6.53–6.43 (2H, ArH), 5.89 (br d, 1H, J=9.4 Hz, NH), 5.14 (dd, 1H, J=5.1, 9.8 Hz, C3-H), 5.10 (s, 2H, OCH$_2$Ph), 4.37 (AB, 2H, J=14.4 Hz, $v_o$δ=36.7 Hz, NCH$_2$Ar), 3.83 (s, 3H, OCH$_3$), 3.81 (s, 3H, OCH$_3$), 3.80–3.49 (m, 2H, CH$_2$OH), 1.94 (m, 1H, OH); $^{13}$C NMR (CDCl$_3$, 62.5 MHz) δ 161.00, 158.16, 131.27, 128.32, 127.91, 104.67, 98.78, 67.14. 58.36, 55.48, 55.3S, 39.65; [α]$_{365}$−150° (c 1.00, CH$_2$Cl$_2$).

EXAMPLE 15

(3R,4R)-3-Carbobenzyloxyamino-4-hydroxymethyl-2-azetidinone

A solution of (3R,4R)-1-(2,4-dimethoxybenzyl)-3-carbobenzyloxyamino-4-hydroxymethyl-2-azetidinone (31.6 mg, 0.081 mmol) in 2.0 mL of 40% aqueous acetonitrile in a 10 mL round-bottom flask equipped with a condenser was deaerated by evacuating (water aspirator) and filling with nitrogen three times. Solid sodium hydrogen phosphate (28.9 mg, 0.202 mmol) and potassium persulfate (33.0 mg, 0.122 mmol) were added and the result was heated to reflux (bath temperature 100° C.). After one hour, additional potassium persulfate (11.0 mg, 0.040 mmol) was added and heating was continued for 30 minutes. The mixture was cooled to room temperature and partitioned between 20 mL each of dichloromethane and water. The aqueous layer was extracted with two 10 mL portions of dichloromethane, and the organic solutions were combined, washed with saturated aqueous sodium chloride, filtered through cotton, and concentrated under reduced pressure. The yellow oil was flash chromatographed (3×10 cm silica gel, 12% isopropanol in dichloromethane, 10 mL fractions) to afford 9.4 mg (46%) of a white solid: $R_f$ 0.18 (10% isopropanol in dichloromethane); IR (CHCl$_3$) 3420, 3380 (broad), 3018, 2918, 1768, 1718, 1518, 1220 cm$^{-1}$; $^1$H NMR (CDCl$_3$, 250 MHz) δ 7.39–7.26 (5H, ArH), 6.76 (s, 1H, azetidinone NH), 6.24 (d, 1H, J=9.9 Hz, CbzNH), 5.16 (dd, 1H, J=4.7, 9.6 Hz, C3-H), 5.09 (s, 2H, OCH$_2$Ph), 3.90–3.40 (4H, C4-H, CH$_2$OH).

I claim:

1. A compound of the formula

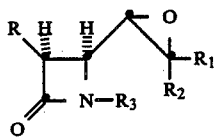

wherein
R is amino or protected amino;
R$_1$ and R$_2$ independently are hydrogen, C$_1$-C$_6$ alkyl, C$_3$-C$_8$ cycloalkyl, —COOR$_3'$ wherein R$_3'$ is a carboxy-protecting group, tri-(C$_1$-C$_4$ alkyl)silyl, tri-(C$_1$-C$_4$ alkyl)silyloxy, cyano, a group of the formula —CH$_2$OR$_3''$ wherein R$_3''$ is C$_1$-C$_4$ alkyl, C$_1$-C$_5$ alkanoyl, C$_1$-C$_4$ alkylsulfonyl or tri-C$_1$-C$_4$ alkyl)silyl; phenyl, naphthyl, or a heteroaryl group selected from thienyl, furyl, benzofuryl, or benzothienyl, or said phenyl, naphthyl or heteroaryl optionally substituted by one or two of the same or different groups selected from among C$_1$-C$_4$ alkyl, C$_1$-C$_4$ alkoxy, halogen, protected amino, di-(C$_1$-C$_4$ alkyl)amino, protected carboxy, C$_1$-C$_5$ alkanoyloxy, C$_1$-C$_4$ alkylsulfonyloxy, C$_1$-C$_4$ alkylsulfonyl, phenylsulfonyl or phenylsulfonyl substituted by C$_1$-C$_4$ alkyl, C$_1$-C$_4$ alkoxy or halogen;
R$_3$ is a nitrogen-protecting group; a substituted methyl group of the formula

wherein R$_4$ is hydrogen, —COOR$_3'$, or a phosphono group of the formula

wherein R$_5$ is C$_1$-C$_4$ alkyl, phenyl, or benzyl and phenyl or benzyl substituted by C$_1$-C$_4$ alkyl, C$_1$-C$_4$ alkoxy or halogen;
and R$_3'$ is a carboxy-protecting group;
or R$_3$ is a β-keto ester derivative of the formula

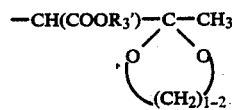

wherein R$_3'$ has the same meaning as defined above.

2. The compound of claim 1 wherein R is amino or protected amino group.

3. The compound of claim 1 wherein R$_1$ and R$_2$ are hydrogen, C$_1$-C$_6$ alkyl, phenyl, —CH$_2$OR$_3''$ or —COOR$_3'$.

4. The compound of claim 1 wherein R$_3$ is a nitrogen-protecting group.

5. The compound of claim 1 wherein R$_3$ is —CH(R$_4$)COOR$_3'$.

6. The compound of claim 1 wherein R$_3$ is

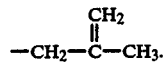

7. The compound of claim 1 in the diastereomeric form of the formula

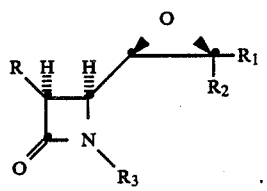

8. The compound of claim 7 wherein R is amino or protected amino.

9. The compound of claim 8 wherein R$_3$ is a nitrogen-protecting group.

10. The compound of claim 9 wherein R is phthalimido, $R_1$ is phenyl, $R_2$ is hydrogen and $R_3$ is 2,4-dimethoxybenzyl.

11. The compound of claim 9 wherein R is benzyloxycarbonylamino, $R_1$ is phenyl, $R_2$ is hydrogen and $R_3$ is 2,4-dimethoxybenzyl.

12. The compound of claim 9 wherein R is phthalimido, $R_1$ and $R_2$ are methyl and $R_3$ is benzyl.

13. The compound of claim 9 wherein R is 4,5-diphenyloxazolin-2-one-3-yl, $R_1$ is phenyl, $R_2$ is hydrogen and $R_3$ is 2,4-dimethoxybenzyl.

14. The compound of claim 8 wherein $R_3$ is —CH$_2$COOR$_3'$.

15. The compound of claim 14 wherein R is phthalimido, $R_1$ is phenyl, $R_2$ is hydrogen and $R_3'$ is t-butyl.

16. The compound of claim 7 wherein R is amino.

17. The compound of claim 1 in the diastereomeric form of the formula

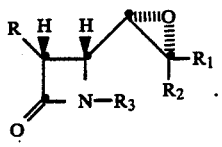

18. The compound of claim 17 wherein R is amino or protected amino group and $R_3$ is a nitrogen-protecting group.

19. The compound of claim 18 wherein R is phthalimido, $R_1$ and $R_2$ are methyl and $R_3$ is benzyl.

20. The compound of claim 17 wherein R is phthalimido, $R_1$ is phenyl, $R_2$ is hydrogen and $R_3$ is benzyl, 2,4-dimethoxybenzyl or 4-methoxybenzyl.

21. The compound of the formula

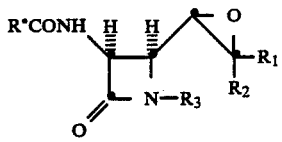

wherein $R^o$ is hydrogen; $C_1$–$C_6$ alkyl, $C_1$–$C_6$ alkyl substituted by cyano, carboxy, halogen, amino, $C_1$–$C_4$ alkoxy, $C_1$–$C_4$ alkylthio, or trifluoromethylthio;
a phenyl or substituted phenyl group represented by the formula

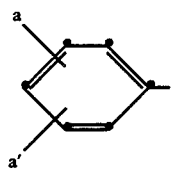

wherein a and a' independently are hydrogen, halogen, hydroxy, $C_1$–$C_4$ alkoxy, $C_1$–$C_4$ alkanoyloxy, $C_1$–$C_4$ alkyl, $C_1$–$C_4$ alkylthio, amino, $C_1$–$C_4$ alkanoylamino, $C_1$–$C_4$ alkylsulfonylamino, carboxy, carbamoyl, aminosulfonyl, hydroxymethyl, aminomethyl, or carboxymethyl;
a group represented by the formula

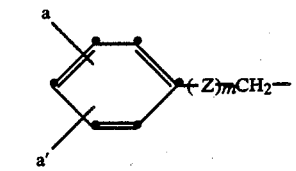

wherein a and a' have the same meanings as defined above, Z is O or S, and m is 0 or 1;
a heteroarylmethyl group represented by the formula

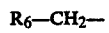

$R_6$—CH$_2$— wherein $R_6$ is thienyl, furyl, benzothienyl, benzofuryl, pyridyl, 4-pyridylthio pyrimidyl, pyridazinyl, indolyl, pyrazolyl, imidazolyl, triazolyl, tetrazolyl, oxazolyl, thiazolyl, oxadiazolyl, thiadiazolyl, and such heteroalkyl groups substituted by amino, hydroxy, halogen $C_1$–$C_4$ alkyl, $C_1$–$C_4$ alkoxy, $C_1$–$C_4$ alkylsulfonylamino;
a substituted methyl group represented by the formula

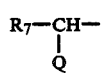

$$R_7-\underset{Q}{\underset{|}{CH}}-$$

wherein $R_7$ is cyclohex-1,4-dienyl, or a phenyl group or substituted phenyl group represented by the formula

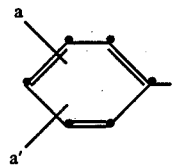

wherein a and a' have the above defined meanings, or $R_7$ is $R_6$ as defined above, and Q is hydroxy, $C_1$–$C_4$ alkanoloxy, carboxy, sulfo, amino, or sulfoamino;
or $R^o$ is a keto group or an oximino-substituted group represented by the formulae

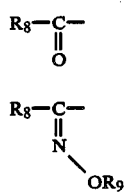

wherein $R_8$ is $R_6$ or $R_7$ as defined above and $R_9$ is hydrogen, $C_1$–$C_4$ alkyl, $C_1$–$C_4$ alkyl substituted by halogen or amino, a group represented by the formula

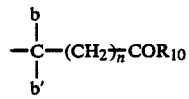

wherein
b and b' independently are hydrogen, or $C_1$–$C_3$ alkyl, n is 0, 1, 2, or 3; and b and b' when taken together with the carbon to which they are bonded form a 3- to 6-membered carbocyclic ring; and $R_{10}$ is hydroxy, $C_1$–$C_4$ alkoxy, amino, $C_1$–$C_4$ alkylamino, or di($C_1$–$C_4$ alkyl)amino;

or $R_9$ is a cyclic lactam represented by the formula

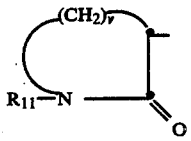

wherein
v is 2, 3, or 4; and $R^6$ is hydrogen or $C_1$–$C_3$ alkyl;

or $R_9$ is a heteroarylmethyl group represented by the formula

$R_6$—$CH_2$— wherein
$R_6$ has the same meanings as defined hereinabove;

$R_1$ and $R_2$ independently are hydrogen, $C_1$–$C_6$ alkyl, $C_3$–$C_8$ cycloalkyl, —COOR$_3$' wherein R$_3$' is a carboxy-protecting group, tri-($C_1$–$C_4$ alkyl)silyl, tri-($C_1$–$C_4$ alkyl)silyloxy, cyano, a group of the formula —$CH_2OR_3$" wherein R$_3$" is $C_1$–$C_4$ alkyl, $C_1$–$C_5$ alkanoyl, $C_1$–$C_4$ alkylsulfonyl or tri-$C_1$–$C_4$ alkyl)silyl; phenyl; naphthyl, or a heteroaryl group selected from thienyl, furyl, benzofuryl, or benzothienyl, or said phenyl, naphthyl or heteroaryl optionally substituted by one or two of the same or different groups selected from among $C_1$–$C_4$ alkyl, $C_1$–$C_4$ alkoxy, halogen, protected amino, di-($C_1$–$C_4$ alkyl)amino, protected carboxy, $C_1$–$C_5$ alkanoyloxy, $C_1$–$C_4$ alkylsulfonyloxy, $C_1$–$C_4$ alkylsulfonyl, phenylsulfonyl or phenylsulfonyl substituted by $C_1$–$C_4$ alkyl, $C_1$–$C_4$ alkoxy or halogen;

$R_3$ is a nitrogen-protecting group; a group of the formula

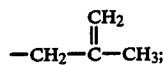

a substituted methyl group of the formula

—CH($R_4$)COOR$_3$' wherein $R_4$ is hydrogen —COOR$_3$' or a phosphono group of the formula

—P(O)(OR$_5$)$_2$ wherein
$R_5$ is $C_2$–$C_4$ alkyl, phenyl, or benzyl and phenyl or benzyl substituted by $C_1$–$C_4$ alkyl, $C_1$–$C_4$ alkoxy or halogen;
and $R_3$' is a carboxy-protecting group;

or $R_3$ is a β-keto ester derivative of the formula

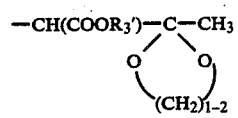

wherein R$_3$' has the same meaning as defined above.

22. The compound of claim 21 wherein $R^o$ is a group of the formula

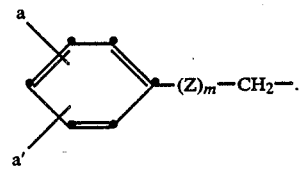

23. The compound of claim 22 wherein $R^o$ is phenoxymethyl or phenylmethyl.

24. The compound of claim 23 wherein $R_1$ and $R_2$ independently are hydrogen, $C_1$–$C_6$ alkyl, phenyl, —COOR$_3$' or —CH$_2$OR$_3$".

* * * * *